(12) United States Patent
Caputo et al.

(10) Patent No.: US 12,367,955 B2
(45) Date of Patent: Jul. 22, 2025

(54) RFID MEDICAL ARTICLE TRACKING SYSTEM AND METHOD

(71) Applicant: MEPS Real-Time, Inc., San Diego, CA (US)

(72) Inventors: Jimmy C. Caputo, San Diego, CA (US); Shariq Hussain, Vista, CA (US); Jeffrey Shamblin, San Marcos, CA (US); James P. Williams, Jr., Carefree, AZ (US); Paul M. Elizondo, II, Escondido, CA (US)

(73) Assignee: MEPS Real-Time, Inc., San Diego, CA (US)

( * ) Notice: Subject to any disclaimer, the term of this patent is extended or adjusted under 35 U.S.C. 154(b) by 0 days.

(21) Appl. No.: 18/594,752

(22) Filed: Mar. 4, 2024

(65) Prior Publication Data
US 2024/0203556 A1 Jun. 20, 2024

Related U.S. Application Data

(63) Continuation of application No. 17/935,366, filed on Sep. 26, 2022, now Pat. No. 11,923,059, which is a (Continued)

(51) Int. Cl.
*G16H 20/10* (2018.01)
*G06K 7/10* (2006.01)
(Continued)

(52) U.S. Cl.
CPC ......... *G16H 20/10* (2018.01); *G06K 7/10168* (2013.01); *G06K 7/10178* (2013.01); *G06K 7/10316* (2013.01); *G06K 7/10356* (2013.01); *G06K 7/10415* (2013.01); *G06Q 10/087* (2013.01); *G06Q 30/00* (2013.01); *G06Q 50/22* (2013.01); *G16H 10/00* (2018.01);
(Continued)

(58) Field of Classification Search
CPC ........ G16H 20/10; G16H 10/00; G16H 10/60; G16H 15/00; G16H 20/00; G16H 40/20; G16H 40/40; G16H 40/63; G06K 7/10168; G06K 7/10178; G06K 7/10316; G06K 7/10356; G06K 7/10415; G06Q 10/087; G06Q 30/00; G06Q 50/22; G16Z 99/00; H01Q 1/22; H01Q 1/2216
See application file for complete search history.

(56) References Cited

U.S. PATENT DOCUMENTS 2,417,542 A 3/1947 Carter
3,443,247 A 5/1969 Fjerstad
(Continued)

*Primary Examiner* — Ryan W Sherwin
(74) *Attorney, Agent, or Firm* — Brooks Kushman PC

(57) ABSTRACT

A system and method for managing the contents of a medical storage container, such as a tray, that has an inventory of medical articles. A Faraday cage enclosure is used to isolate, scan, and inventory the container. The container and each of the medical articles in the container have a respective RFID tag. A processor is programmed to retrieve the inventory list for the container based on its RFID tag and compare the actual contents of the container according to their tags to the inventory list. The processor is also programmed to show the layout of the pockets of a tray and show an indicator of which pocket a particular medical article should be located.

17 Claims, 22 Drawing Sheets

Related U.S. Application Data continuation of application No. 16/877,242, filed on May 18, 2020, now Pat. No. 11,456,066, which is a continuation of application No. 16/278,653, filed on Feb. 18, 2019, now Pat. No. 10,658,078, which is a continuation of application No. 15/838,310, filed on Dec. 11, 2017, now Pat. No. 10,210,954, which is a continuation of application No. 14/943,010, filed on Nov. 16, 2015, now Pat. No. 9,842,189, which is a continuation of application No. 14/214,284, filed on Mar. 14, 2014, now Pat. No. 9,189,769, which is a continuation-in-part of application No. 13/776,613, filed on Feb. 25, 2013, now Pat. No. 8,686,859, which is a continuation of application No. 12/631,861, filed on Dec. 7, 2009, now Pat. No. 8,384,545.

(60) Provisional application No. 61/800,803, filed on Mar. 15, 2013.

(51) Int. Cl.
| | | |
|---|---|---|
| *G06Q 10/087* | (2023.01) | |
| *G06Q 30/00* | (2023.01) | |
| *G06Q 50/22* | (2018.01) | |
| *G16H 10/00* | (2018.01) | |
| *G16H 10/60* | (2018.01) | |
| *G16H 15/00* | (2018.01) | |
| *G16H 20/00* | (2018.01) | |
| *G16H 40/20* | (2018.01) | |
| *G16H 40/40* | (2018.01) | |
| *G16H 40/63* | (2018.01) | |
| *G16Z 99/00* | (2019.01) | |
| *H01Q 1/22* | (2006.01) | |

(52) U.S. Cl.
CPC ............. *G16H 10/60* (2018.01); *G16H 15/00* (2018.01); *G16H 20/00* (2018.01); *G16H 40/20* (2018.01); *G16H 40/40* (2018.01); *G16H 40/63* (2018.01); *G16Z 99/00* (2019.02); *H01Q 1/22* (2013.01); *H01Q 1/2216* (2013.01)

(56) References Cited

U.S. PATENT DOCUMENTS

| | | |
|---|---|---|
| 4,293,223 A | 10/1981 | Seaton |
| 4,349,798 A | 9/1982 | Podell et al. |
| 4,495,478 A | 1/1985 | Kwon et al. |
| 5,581,268 A | 12/1996 | Hirshfield |
| 5,654,508 A | 8/1997 | Gibbs |
| 5,936,527 A | 8/1999 | Isaacman et al. |
| 5,977,875 A | 11/1999 | Lin et al. |
| 6,133,800 A | 10/2000 | Deng |
| 6,232,870 B1 | 5/2001 | Garber et al. |
| 6,304,182 B1 | 10/2001 | Mori et al. |
| 6,486,780 B1 | 11/2002 | Garber et al. |
| 6,677,857 B2 | 1/2004 | Bara et al. |
| 6,703,935 B1 | 7/2004 | Chung et al. |
| 6,768,472 B2 | 7/2004 | Alexopoulos et al. |
| 6,996,543 B1 | 2/2006 | Coppersmith et al. |
| 7,095,326 B2 | 8/2006 | Young et al. |
| 7,155,306 B2 | 12/2006 | Haitin et al. |
| 7,175,081 B2 | 2/2007 | Andreasson et al. |
| 7,178,729 B2 | 2/2007 | Shaffer et al. |
| 7,258,276 B2 | 8/2007 | Linton et al. |
| 7,293,705 B2 | 11/2007 | Linton et al. |
| 7,299,981 B2 | 11/2007 | Hickle et al. |
| 7,369,919 B2 | 5/2008 | Vonk et al. |
| 7,433,610 B2 | 10/2008 | Oyama |
| 7,448,544 B1 | 11/2008 | Louie et al. |
| 7,466,232 B2 | 12/2008 | Neuwirth |
| 7,518,516 B2 | 4/2009 | Azevedo et al. |
| 7,639,136 B1 | 12/2009 | Wass et al. |
| 7,932,824 B2 | 4/2011 | Flores et al. |
| 8,031,124 B2 | 10/2011 | Kato et al. |
| 8,085,150 B2 | 12/2011 | Oberle |
| 8,174,392 B1 | 5/2012 | Saghbini et al. |
| 8,215,549 B2 | 7/2012 | Arpino |
| 8,313,024 B2 | 11/2012 | Marino |
| 8,332,240 B1 | 12/2012 | Garver et al. |
| 8,341,041 B2 | 12/2012 | Hull |
| 8,384,545 B2 | 2/2013 | Hussain et al. |
| 8,686,859 B2 | 4/2014 | Hussain et al. |
| 9,189,769 B2 | 11/2015 | Caputo et al. |
| 9,205,886 B1* | 12/2015 | Hickman ............. G05D 1/0246 |
| 9,842,189 B2 | 12/2017 | Caputo et al. |
| 10,210,954 B2 | 2/2019 | Caputo et al. |
| 10,621,394 B2 | 4/2020 | Hussain et al. |
| 10,658,078 B2 | 5/2020 | Caputo et al. |
| 11,144,737 B2 | 10/2021 | Hussain et al. |
| 2001/0045373 A1* | 11/2001 | Peterson ................. A61J 7/04 206/534 |
| 2003/0154141 A1* | 8/2003 | Capazario ............ G06Q 10/087 705/26.1 |
| 2004/0008123 A1 | 1/2004 | Carrender et al. |
| 2004/0046020 A1 | 3/2004 | Andreasson et al. |
| 2005/0088306 A1 | 4/2005 | Andreasson et al. |
| 2005/0108057 A1 | 5/2005 | Cohen et al. |
| 2006/0015543 A1* | 1/2006 | Humphrey ............ G01F 15/061 |
| 2006/0192001 A1 | 8/2006 | Shaffer et al. |
| 2007/0001809 A1 | 1/2007 | Kodukula et al. |
| 2007/0001890 A1 | 1/2007 | Piasecki et al. |
| 2007/0050272 A1 | 3/2007 | Godlewski et al. |
| 2007/0125442 A1 | 6/2007 | Tribble et al. |
| 2007/0135965 A1 | 6/2007 | Nguyen et al. |
| 2007/0150382 A1 | 6/2007 | Danilewitz |
| 2007/0210923 A1 | 9/2007 | Butler et al. |
| 2007/0257857 A1 | 11/2007 | Marino et al. |
| 2007/0258048 A1 | 11/2007 | Pitchers |
| 2007/0272746 A1 | 11/2007 | Ortiz et al. |
| 2008/0001746 A1 | 1/2008 | Childress et al. |
| 2008/0001748 A1* | 1/2008 | Childress ............... G06K 17/00 700/214 |
| 2008/0018475 A1 | 1/2008 | Breed et al. |
| 2008/0065264 A1 | 3/2008 | Omura et al. |
| 2008/0093448 A1 | 4/2008 | de la Huerga |
| 2008/0094214 A1 | 4/2008 | Azevedo et al. |
| 2008/0094222 A1 | 4/2008 | Kaoru |
| 2008/0117048 A1 | 5/2008 | Rachwalski et al. |
| 2008/0129453 A1 | 6/2008 | Shanks |
| 2008/0172253 A1 | 7/2008 | Chung et al. |
| 2008/0224831 A1 | 9/2008 | Arai et al. |
| 2008/0224875 A1 | 9/2008 | Phillips et al. |
| 2008/0231426 A1* | 9/2008 | Kamel ................. G06Q 10/087 340/10.4 |
| 2008/0283596 A1 | 11/2008 | Ishida |
| 2008/0283597 A1 | 11/2008 | Massod |
| 2008/0316045 A1 | 12/2008 | Sriharto et al. |
| 2008/0319790 A1 | 12/2008 | Valberg et al. |
| 2009/0037244 A1* | 2/2009 | Pemberton ........... G06Q 10/087 705/28 |
| 2009/0128299 A1 | 5/2009 | Kirmeier et al. |
| 2009/0267772 A1 | 10/2009 | Dehnadi |
| 2010/0010666 A1 | 1/2010 | Adams |
| 2010/0036755 A1 | 2/2010 | Saghbini |
| 2010/0161435 A1 | 6/2010 | Shimizu et al. |
| 2011/0010275 A1 | 1/2011 | Hull |
| 2011/0221577 A1 | 9/2011 | Kuwako et al. |
| 2012/0137706 A1 | 6/2012 | Hussain et al. |
| 2012/0161967 A1* | 6/2012 | Stern ................... G06Q 10/087 340/572.1 |
| 2013/0035950 A1 | 2/2013 | MacDonald et al. |
| 2014/0172651 A1* | 6/2014 | Flori ................. G06Q 10/087 705/28 |

* cited by examiner

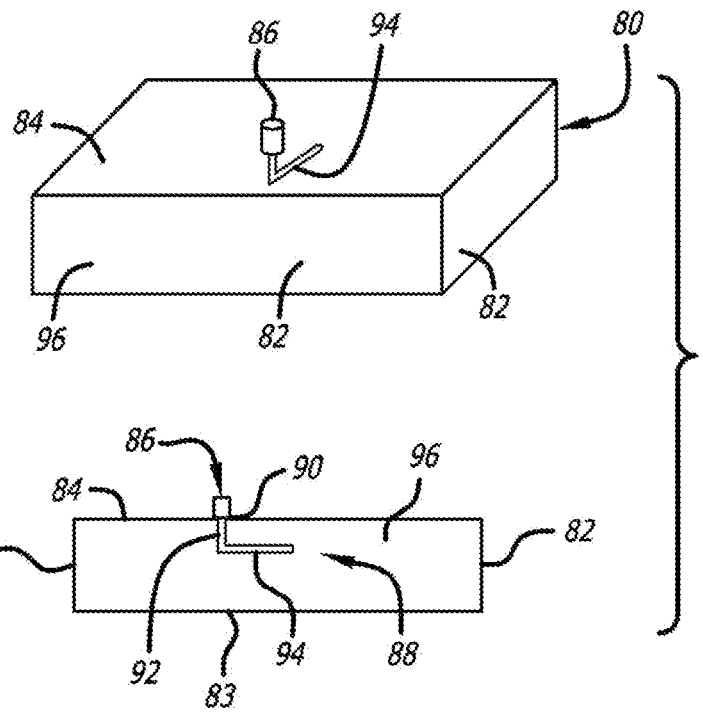
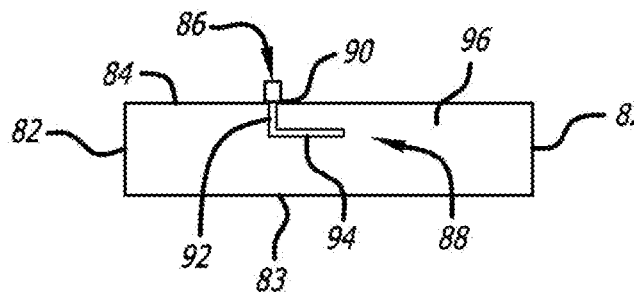
FIG. 5
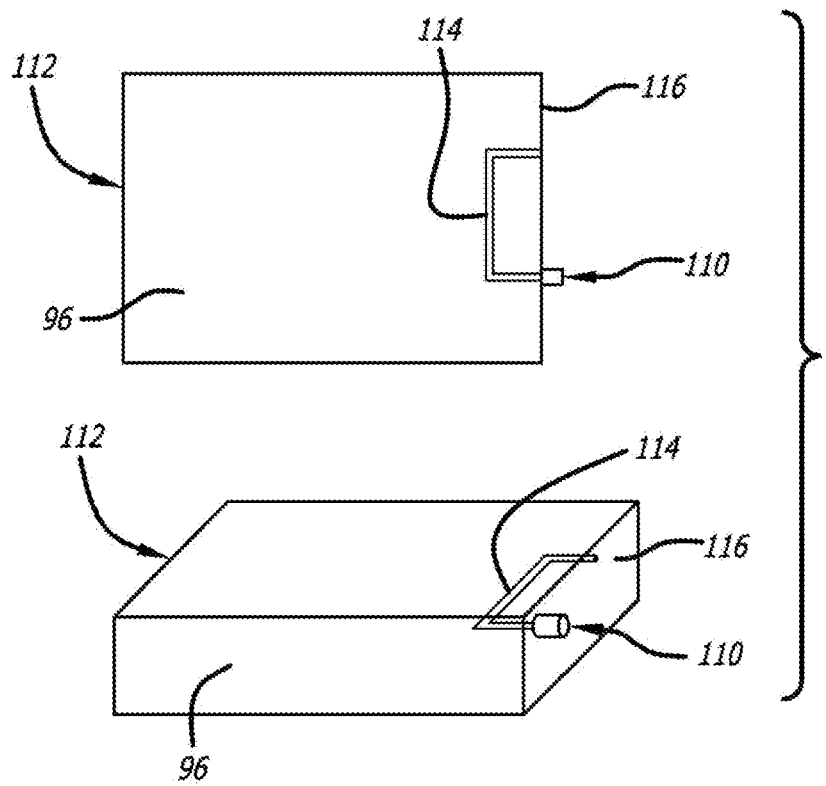
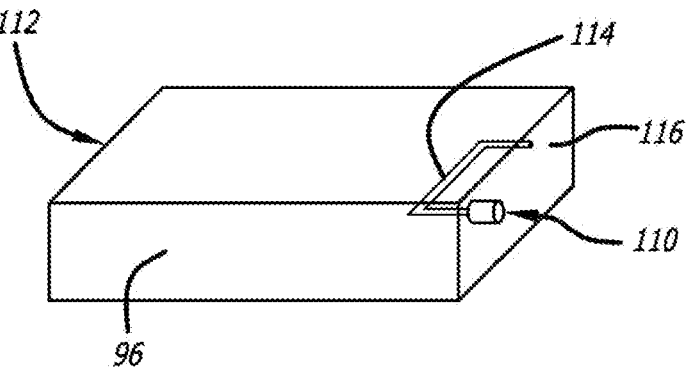
FIG. 6

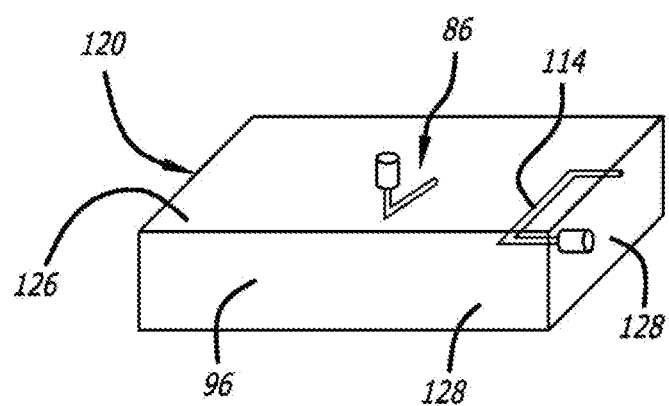
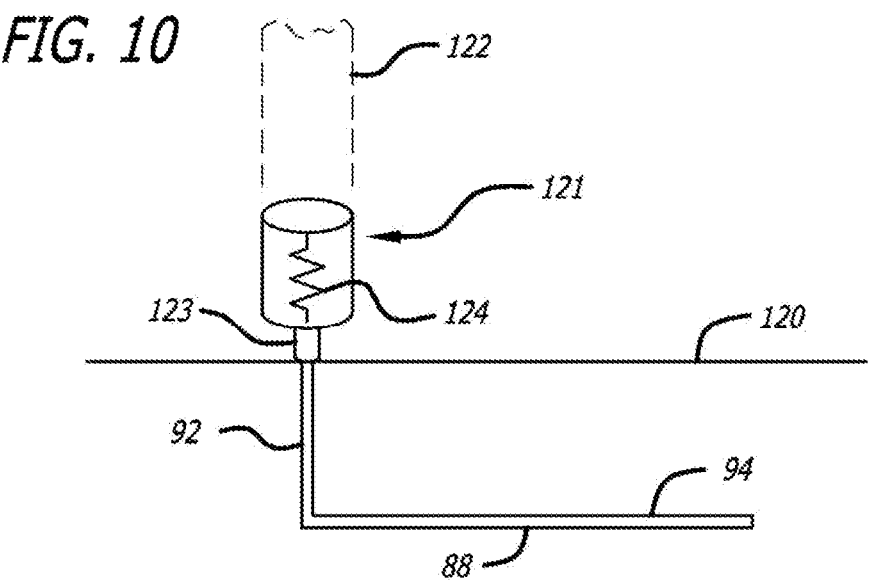

*If desired, replace items expiring within ___ days.*

| | | | | |
|---|---|---|---|---|
| 1 | | | | |
| 10 | | | | |
| 20 | | | | |
| 30 | | | | |
| 40 | | | | |
| 60 | ~ 552 | | | |
| 90 | | | | |

Item Name    Manufacturer    Lot #    Expiration Date    Quantity

RFID MEDICAL ARTICLE TRACKING SYSTEM AND METHOD

CROSS-REFERENCES TO RELATED APPLICATIONS

This application is a continuation of U.S. application Ser. No. 17/935,366 filed Sep. 26, 2022, which is a continuation of U.S. application Ser. No. 16/877,242 filed May 18, 2020 now U.S. Pat. No. 11,456,066, which is a continuation of U.S. application Ser. No. 16/278,653 filed Feb. 18, 2019 now U.S. Pat. No. 10,658,078, which is a continuation of U.S. application Ser. No. 15/838,310, filed Dec. 11, 2017, now U.S. Pat. No. 10,210,954, which is a continuation of U.S. application Ser. No. 14/943,010, filed Nov. 16, 2015, now U.S. Pat. No. 9,842,189, which is a continuation of U.S. application Ser. No. 14/214,284, filed Mar. 14, 2014, now U.S. Pat. No. 9,189,769, which is a continuation-in-part of U.S. application Ser. No. 13/776,613 filed Feb. 25, 2013, now U.S. Pat. No. 8,686,859, which is a continuation of U.S. application Ser. No. 12/631,861, filed Dec. 7, 2009, now U.S. Pat. No. 8,384,545 and application Ser. No. 14/214,284 also claims the benefit of U.S. Provisional Application No. 61/800,803, filed Mar. 15, 2013. All of the above documents are incorporated herein by reference.

BACKGROUND

The invention relates generally to the field of wireless identification of medical articles in a healthcare setting, and more particularly, to a system and method for managing the inventory of medical article containers.

There are a number of ways of identifying and tracking articles including visually, optically (bar coding, for example), magnetically, RFID, weighing, and others. Where an automatic system for tracking is desired, RFID is a candidate since identification data may be obtained wirelessly. RFID tags have decreased in cost, which has made them even more attractive for such an application.

Radio-frequency identification ("RFID") is the use of electromagnetic energy ("EM energy") to stimulate a responsive device (known as an RFID "tag" or transponder) to identify itself and in some cases, provide additionally stored data. RFID tags typically include a semiconductor device having a memory, circuitry, and one or more conductive traces that form an antenna. Typically, RFID tags act as transponders, providing information stored in the semiconductor device memory in response to an RF interrogation signal received from a reader, also referred to as an interrogator. Some RFID tags include security measures, such as passwords and/or encryption. Many RFID tags also permit information to be written or stored in the semiconductor memory via an RF signal.

RFID tags may be incorporated into or attached to articles to be tracked. In some cases, the tag may be attached to the outside of an article with adhesive, tape, or other means and in other cases, the tag may be inserted within the article, such as being included in the packaging, located within the container of the article, or sewn into a garment. The RFID tags are manufactured with a unique identification number which is typically a simple serial number of a few bytes with a check digit attached. This identification number is incorporated into the tag during manufacture. The user cannot alter this serial/identification number and manufacturers guarantee that each serial number is used only once. This configuration represents the low cost end of the technology in that the RFID tag is read-only and it responds to an interrogation signal only with its identification number. Typically, the tag continuously responds with its identification number. Data transmission to the tag is not possible. These tags are very low cost and are produced in enormous quantities.

Such read-only RFID tags typically are permanently attached to an article to be tracked and, once attached, the serial number of the tag is associated with its host article in a computer database. For example, a particular type of medicine may be contained in hundreds or thousands of small vials. Upon manufacture, or receipt of the vials at a health care institution, an RFID tag is attached to each vial. Each vial with its permanently attached RFID tag will be checked into the database of the health care institution upon receipt. The RFID identification number may be associated in the database with the type of medicine, size of the dose in the vial, and perhaps other information such as the expiration date of the medicine. Thereafter, when the RFID tag of a vial is interrogated and its identification number read, the database of the health care institution can match that identification number with its stored data about the vial. The contents of the vial can then be determined as well as any other characteristics that have been stored in the database. This system requires that the institution maintain a comprehensive database regarding the articles in inventory rather than incorporating such data into an RFID tag.

An object of the tag is to associate it with an article throughout the article's life in a particular facility, such as a manufacturing facility, a transport vehicle, a health care facility, a storage area, or other, so that the article may be located, identified, and tracked, as it is moved. For example, knowing where certain medical articles reside at all times in a health care facility can greatly facilitate locating needed medical supplies when emergencies arise. Similarly, tracking the articles through the facility can assist in generating more efficient dispensing and inventory control systems as well as improving work flow in a facility. Additionally, expiration dates can be monitored and those articles that are older and about to expire can be moved to the front of the line for immediate dispensing. This results in better inventory control and lowered costs.

Other RFID tags are writable and information about the article to which the RFID tag is attached can be programmed into the individual tag. While this can provide a distinct advantage when a facility's computer servers are unavailable, such tags cost more, depending on the size of the memory in the tag. Programming each one of the tags with information contained in the article to which they are attached involves further expense.

RFID tags may be applied to containers or articles to be tracked by the manufacturer, the receiving party, or others. In some cases where a manufacturer applies the tags to the product, the manufacturer will also supply a respective database file that links the identification number of each of the tags to the contents of each respective article. That manufacturer supplied database can be distributed to the customer in the form of a file that may easily be imported into the customer's overall database thereby saving the customer from the expense of creating the database.

Many RFID tags used today are passive in that they do not have a battery or other autonomous power supply and instead, must rely on the interrogating energy provided by an RFID reader to provide power to activate the tag. Passive RFID tags require an electromagnetic field of energy of a certain frequency range and certain minimum intensity in order to achieve activation of the tag and transmission of its stored data. Another choice is an active RFID tag; however, such tags require an accompanying battery to provide power to activate the tag, thus increasing the expense of the tag and making them undesirable for use in a large number of applications.

Depending on the requirements of the RFID tag application, such as the physical size of the articles to be identified, their location, and the ability to reach them easily, tags may need to be read from a short distance or a long distance by an RFID reader. Such distances may vary from a few centimeters to ten or more meters. Additionally, in the U.S. and in other countries, the frequency range within which such tags are permitted to operate is limited. As an example, lower frequency bands, such as 125 KHz and 13.56 MHz, may be used for RFID tags in some applications. At this frequency range, the electromagnetic energy is less affected by liquids and other dielectric materials, but suffers from the limitation of a short interrogating distance. At higher frequency bands where RFID use is permitted, such as 915 MHz and 2.4 GHZ, the RFID tags can be interrogated at longer distances, but they de-tune more rapidly as the material to which the tag is attached varies. It has also been found that at these higher frequencies, closely spaced RFID tags will de-tune each other as the spacing between tags is decreased.

There are a number of common situations where the RFID tags may be located inside enclosures. Some of these enclosures may have entirely or partially metal or metallized surfaces. Examples of enclosures include metal enclosures (e.g., shipping containers), partial metal enclosures (e.g., vehicles such as airplanes, buses, trains, and ships that have a housing made from a combination of metal and other materials), and non-metal enclosures (e.g., warehouses and buildings made of wood). Examples of objects with RFID tags that may be located in these enclosures include loose articles, packaged articles, parcels inside warehouses, inventory articles inside buildings, various goods inside retail stores, and various portable articles (e.g., passenger identification cards and tickets, baggage, cargo, individual life-saving equipment such as life jackets and masks) inside vehicles, etc.

The read range (i.e., the range of the interrogation and/or response signals) of RFID tags is limited. For example, some types of passive RFID tags have a maximum range of about twelve meters, which may be attained only in ideal free space conditions with favorable antenna orientation. In a real situation, the observed tag range is often six meters or less. Therefore, some of the enclosures described above may have dimensions that far exceed the read range of an individual RFID tag. Unless the RFID reader can be placed in close proximity to a target RFID tag in such an enclosure, the tag will not be activated and read. Additionally, metal surfaces of the enclosures present a serious obstacle for the RF signals that need to be exchanged between RFID readers and RFID tags, making RFID tags located behind those metal surfaces difficult or impossible to detect.

In addition to the above, the detection range of the RFID systems is typically limited by signal strength to short ranges, frequently less than about thirty centimeters for 13.56 MHZ systems. Therefore, portable reader units may need to be moved past a group of tagged items in order to detect all the tagged items, particularly where the tagged items are stored in a space significantly greater than the detection range of a stationary or fixed single reader antenna. Alternately, a large reader antenna with sufficient power and range to detect a larger number of tagged items may be used. However, such an antenna may be unwieldy and may increase the range of the radiated power beyond allowable limits. Furthermore, these reader antennae are often located in stores or other locations where space is at a premium and it is expensive and inconvenient to use such large reader antennae. In another possible solution, multiple small antennae may be used but such a configuration may be awkward to set up when space is at a premium and when wiring is preferred or required to be hidden.

In the case of medical supplies and devices, it is desirable to develop accurate tracking, inventory control systems, and dispensing systems so that RFID tagged devices and articles may be located quickly should the need arise, and may be identified for other purposes, such as expiration dates. In the case of medical supply or dispensing cabinets used in a health care facility, a large number of medical devices and articles are located closely together, such as in a plurality of drawers. Cabinets such as these are typically made of metal, which can make the use of an external RFID system for identification of the stored articles difficult. In some cases, such cabinets are locked due to the presence of narcotics or other medical articles or apparatus within them that are subject to a high theft rate. Thus, manual identification of the cabinet contents is difficult due to the need to control access.

Providing an internal RFID system in such a cabinet can pose challenges. Where internal articles can have random placement within the cabinet, the RFID system must be such that there are no "dead zones" that the RFID system is unable to reach. In general, dead zones are areas in which the level of coupling between an RFID reader antenna and an RFID tag is not adequate for the system to perform a successful read of the tag. The existence of such dead zones may be caused by orientations in which the tag and the reader antennae are in orthogonal planes. Thus, articles placed in dead zones may not be detected thereby resulting in inaccurate tracking of tagged articles.

Often in the medical field, there is a need to read a large number of tags attached to articles in such an enclosure, and as mentioned above, such enclosures have limited access due to security reasons. The physical dimension of the enclosure may need to vary to accommodate a large number of articles or articles of different sizes and shapes. In order to obtain an accurate identification and count of such closely-located medical articles or devices, a robust electromagnetic energy field must be provided at the appropriate frequency within the enclosure to surround all such stored articles and devices to be sure that their tags are all are activated and read. Such medical devices may have the RFID tags attached to the outside of their containers and may be stored in various orientations with the RFID tag (and associated antenna) pointed upwards, sideways, downward, or at some other angle in a random pattern.

Generating such a robust EM energy field is not an easy task. Where the enclosure has a size that is resonant at the frequency of operation, it can be easier to generate a robust EM field since a resonant standing wave may be generated within the enclosure. However, in the RFID field the usable frequencies of operation are strictly controlled and are limited. It has been found that enclosures are desired for the storage of certain articles that do not have a resonant frequency that matches one of the allowed RFID frequencies. Thus, a robust EM field must be established in another way.

Additionally, where EM energy is introduced to such an enclosure for reading the RFID tags within, efficient energy transfer is of importance. Under static conditions, the input or injection of EM energy into an enclosure can be maximized with a simple impedance matching circuit positioned between the conductor delivering the energy and the enclosure. As is well known to those of skill in the art, such impedance matching circuits or devices maximize the power transfer to the enclosure while minimizing the reflections of power from the enclosure. Where the enclosure impedance changes due to the introduction or removal of articles to or from the enclosure, a static impedance matching circuit may not provide optimum energy transfer into the enclosure. If the energy transfer and resulting RF field intensity within the enclosure were to fall below a threshold level, some or many of the tags on articles within the enclosure would not be activated to identify themselves, leaving an ineffective inventory system.

It is a goal of many health care facilities to keep the use of EM energy to a minimum, or at least contained. The use of high-power readers to locate and extract data from RFID tags is generally undesirable in health care facilities, although it may be acceptable in warehouses that are sparsely populated with workers, or in aircraft cargo holds. Radiating a broad beam of EM energy at a large area, where that EM energy may stray into adjacent, more sensitive areas, is undesirable. Efficiency in operating a reader to obtain the needed identification information from tags is an objective. In many cases where RFID tags are read, handheld readers are used. Such readers transmit a relatively wide beam of energy to reach all RFID tags in a particular location. While the end result of activating each tag and reading it may be accomplished, the transmission of the energy is not controlled except by the aim of the user. Additionally, this is a manual system that will require the services of one or more individuals, which can also be undesirable in facilities where staff is limited.

In a healthcare environment, there are many storage systems for key medical articles that are used for different purposes. Some are open access storage systems. In most of these cases, and especially for emergency storage systems, they must be restocked upon use on a priority basis. Examples of such emergency storage systems are "crash carts," "anesthesia carts," and others. See FIG. 23 for an example of a crash cart 300. Such carts usually include wheels 302 so that they are mobile and may have multiple drawers 304 in which various medical articles are stored. An external handle 306 is provided to assist in handling the cart 300. Access to these carts must be immediate and unhindered, and controlled access is not required. Upon usage of any item in the cart, the cart must be fully inventoried for resupply. This takes a significant amount of time to accomplish correctly. The need to have these carts immediately available for use requires action from the pharmacy in a timely manner. Upon resupply, the carts are usually sealed and placed in strategic locations within the healthcare facility for immediate access.

Another type of storage system is commonly known as a tray or code tray, and may have other names. The code is typically used to identify the medical purpose of the tray, such as a "code blue" tray to resuscitate a person undergoing cardiac arrest. Such a tray may be formed of non-metallic material such as composites or plastics. The tray holds all of the medications, tools, and equipment that are expected to be required to complete a medical procedure or to handle a particular medical event.

A tray is typically laid out and displayed in an easily recognizable fashion. Color may be used also to assist in managing the inventory of the tray. This allows an assistant to retrieve the correct medication or instrument without delay. In the event that a surgeon is looking for the optimum tool or medication, a quick glance at the surgical tray will allow the identification of all available tools at his or her disposal. Labels are often placed on the tray also that specify what is in the pockets of the tray.

An example of such a medical "tray" is shown in FIG. 24. The tray 320 is a single layer and includes various pharmaceuticals 322 and other medical articles, such as pre-loaded syringes 324 (epinephrine syringe, lidocaine syringe, and an atropine syringe). The entire tray is sealed with clear plastic wrap 326 and an inventory list 328 is contained just under the plastic seal so that it is visible and readable without breaking the seal. The Required Inventory list in this case identifies the name of the tray, such as "Childbirth Tray," lists the contents of the tray, and includes other information such as the first expiration date of any of the articles contained in the tray. The Required Inventory list may also contain a plan layout of the tray showing which articles should be stored where. It may have multiple pages or only a single page.

The tray 320 has been prepared by a pharmacist at the pharmacy because it has prescription medications in it (oxytocin for example). The Required Inventory list may also include brand names as well as generic names, and National Drug Codes ("NDCs") or Universal Product Codes ("UPCs") as part of the inventory. State regulations typically allow a hospital or other facility to define the contents of its trays, and therefore they can be selected based on particular "community" standards and requirements. State regulations, typically require that the hospital have specific procedures to ensure accuracy of tray contents. Such procedures include inventory and restocking procedures, as well as detection of expired and recalled medical articles. In the example of FIG. 24, the tray is relatively small. However for other purposes, a tray can be much larger with many more medical articles. Some trays may include additional layers that include additional items not contained in the top layer.

If the seal is broken, regardless of whether any of the contents were removed, an inventory will likely be required. Existing processes require that this be done manually. Each of the articles in the tray is examined to determine if it is expired or recalled, and is compared against the Required Inventory list to determine if it should be in the tray. The Required Inventory list is also referenced for checking that all required articles are in the tray and that extra articles are not in the tray. Once it has been restocked, the tray 320 is rescaled 326 and may be placed on the floor again for medical use. Such examination and restocking can take significant amounts of time and if a pharmacist is required to perform some of the inventory process, that pharmacist will be unavailable to perform other duties. In such a manual procedure, mistakes can be made. Thus, a need has been identified to provide a more efficient and accurate system and method to restock such carts and trays.

Crash carts and trays must be resupplied periodically to replace expired or recalled items, and if a cart or a tray was actually used, to replace consumed articles. As mentioned, such processes are typically performed manually at a significant cost in time. Missing key medical articles in a tray could be devastating in an emergency situation. Therefore accuracy in the resupply is mandatory. Often, trays that have articles that are just nearing expiration must be returned to the pharmacy for resupply in advance of expiration due to the time it takes to process the tray. Any recalled articles must also be removed and substitutions made. It is also possible that items foreign to the crash cart or tray have been added while they were in the field, and these foreign articles must be found and removed.

Unfortunately, the above procedures tend to suffer from significant shortcomings. For instance, manual inspections can result in errors as can resupply. Creating records of what was done is also generally time consuming and error prone, all of which drive up the cost of creating and resupplying the carts and trays. There has therefore been recognized a need for improvement in managing such crash carts and trays.

Furthermore, under the current system, the pharmacy is unable to create individualized carts for patients. For example, certain patients may be provided a patient-specific cocktail of drugs (this may be a mixed vial or a combination of drugs). Because these are non-standard drugs or drug combinations, a pharmacist has to double check a drug list or a prescription list when creating a cocktail drug or filling a personalized cart with medical items.

Hence, those skilled in the art have recognized a need for an improved real-time inventory system for managing medical article container systems. Additionally, a need has been recognized for performing such article management with a more compact, self-contained wireless reader system that reduces the space needed to inventory crash carts and trays. A further need has been recognized for confining the energy used for reading wireless medical article identification devices to a particular area so that accuracy of identification is obtained. The present invention fulfills these needs and others.

SUMMARY OF THE INVENTION

Briefly and generally there is provided a system and a method to manage the inventories of medical article storage containers, including trays and crash carts. In a first aspect, there is provided a medical container re-supply system for reading a data carrier that is attached to a medical container and a data carrier attached to a medical article located in the storage container to manage the inventory of the storage container, the data carrier being responsive to electromagnetic energy (EM) of a frequency f1 in response to which the data carrier provides identification data, the system comprising a metallic enclosure having an internal storage area, the metallic enclosure further having electrically conductive walls that completely surround the internal storage area and any medical article with associated data carrier placed therein, the enclosure having a natural frequency of resonance f2 which is different from a frequency f1 and to which a data carrier that is responsive to frequency f1 is not responsive, a probe disposed at a metallic wall of the metallic enclosure within the metallic enclosure, the probe configured to inject electromagnetic energy of a frequency f1 into the metallic enclosure, wherein the position of the probe in relation to the metallic walls of the metallic enclosure is selected so that reflected EM of frequency f1 within the metallic enclosure is in phase at the probe position to thereby optimize power transfer at frequency f1 into the enclosure, an active impedance matching circuit coupled to the probe and configured to actively more closely match impedance of the probe to impedance of the metallic enclosure at frequency f1, a storage container having a data carrier identifying the container, the container being located within the internal storage area of the metallic enclosure and containing a medical article with an associated data carrier identifying that medical article, both data carriers being responsive to EM at frequency f1 but not operationally responsive to frequency f2, a receiving antenna disposed within the metallic enclosure and configured to receive the identification data provided by the data carrier, a predetermined required inventory list of medical articles for the storage container, a non-volatile memory on which is stored the inventory list of the storage container, a processor programmed to receive the identification data of the storage container and the identification data of the article in the storage container, locate the storage container inventory list in the memory through the identification of the storage container, locate the details of the medical article in the storage container in the memory through the identification data of the medical article, and compare the details of the medical article against the required inventory list of the storage container to manage the inventory of the container.

In more detailed aspects, the processor is also configured to determine if the article in the storage container is expired through locating the details of the medical article, including its expiration date, from the memory, comparing that expiration date to the present date, and providing a notice of expiration if the two dates match or if the expiration date of the medical article preceded the present date. The memory includes a database in which the details of recalled items are contained, and the processor further being programmed to compare the details of the medical article in the storage container to the recalled article database on the memory, and if the comparison shows that the medical article is recalled, to provide an indication of such recall status.

In a method aspect in accordance with the invention, there is provided a method of resupplying a medical container by reading a data carrier that is attached to the medical container and a data carrier attached to a medical article located in the storage container to manage the inventory of the storage container, the data carrier having a specified operation frequency f1 in response to which the data carrier provides identification data, the medical container and medical article being located within an internal storage area of a metallic enclosure, the metallic enclosure further having electrically conductive walls that completely surround the internal storage area and any medical article with associated data carrier placed therein, the metallic enclosure having a natural frequency of resonance f2 which is a frequency other than the specified operation frequency f1 of the data carrier, the method comprising positioning a storage container within the internal storage area of the enclosure, the storage container having a data carrier identifying the container, the container containing a medical article with an associated data carrier identifying that medical article, both data carriers being responsive to EM at frequency f1 but not operationally responsive to frequency f2, injecting electromagnetic ("EM") energy of a frequency $f_1$ into the metallic enclosure from a location within the enclosure, the injecting location being selected in relation to the metallic walls so that reflected energy of frequency f1 within the metallic enclosure is in phase at the location of injection to thereby optimize power transfer of EM energy at frequency $f_1$ into the enclosure, actively matching an impedance associated with injecting the EM energy into the metallic enclosure to more closely match an impedance of the metallic enclosure at frequency f1. receiving identification data provided by a data carrier located within the internal storage area of the metallic enclosure by means of an antenna disposed within the metallic enclosure, storing a predetermined required inventory list of the storage container on a non-volatile memory, receiving the identification data of the storage container and the identification data of the article in the storage container by a processor, locating the storage container inventory in the memory by the processor through the identification of the storage container, locating the details of the medical article in the storage container by the processor in the memory through the identification data of the medical article, and comparing the details of the medical article against the required inventory list of the storage container to manage the inventory of the container.

In more detailed aspects, the method further comprises determining by the processor if the article in the storage container is expired through locating the details of the medical article, including its expiration date, from the memory, comparing that expiration date to the present date, and providing a notice of expiration if the two dates match or if the expiration date of the medical article preceded the present date. Also included is the aspect of comparing the details of the medical article in the storage container to a recalled article database on the memory, and if the comparison shows that the medical article is recalled, providing an indication of such recall status about the medical article.

The features and advantages of the invention will be more readily understood from the following detailed description that should be read in conjunction with the accompanying drawings.

BRIEF DESCRIPTION OF THE DRAWINGS

FIG. 5 shows an enclosure with a single probe and a connector, the probe being configured to inject EM energy into the enclosure and excite a TE mode;

FIG. 6 shows an enclosure with a single probe and a connector, the probe being configured to inject EM energy into the enclosure and excite a TM mode;

FIG. 9 shows an enclosure with two probes each with a connector for injecting EM energy into the enclosure, one probe being a TM probe and the other being a TE probe;

FIG. 10 shows a probe, a connector, and an attenuator that is used to improve the impedance match between the probe and the enclosure;

FIG. 30 shows a program feature in which the method of FIG. 29 may be controlled to search for expired articles within a selected time period;

FIG. 31 shows a program feature in which a graphic may be displayed showing the layout of a particular tray and showing a blinking indicator (asterisk in this case) that shows in which pocket a particular medical article is or should be placed; and FIG. 32 shows a program feature in which the results of scanning a tray are displayed with lists multiple categories of the contents, such as expired, recalled, missing, and others.

DETAILED DESCRIPTION OF THE PREFERRED EMBODIMENTS

Figure 1:
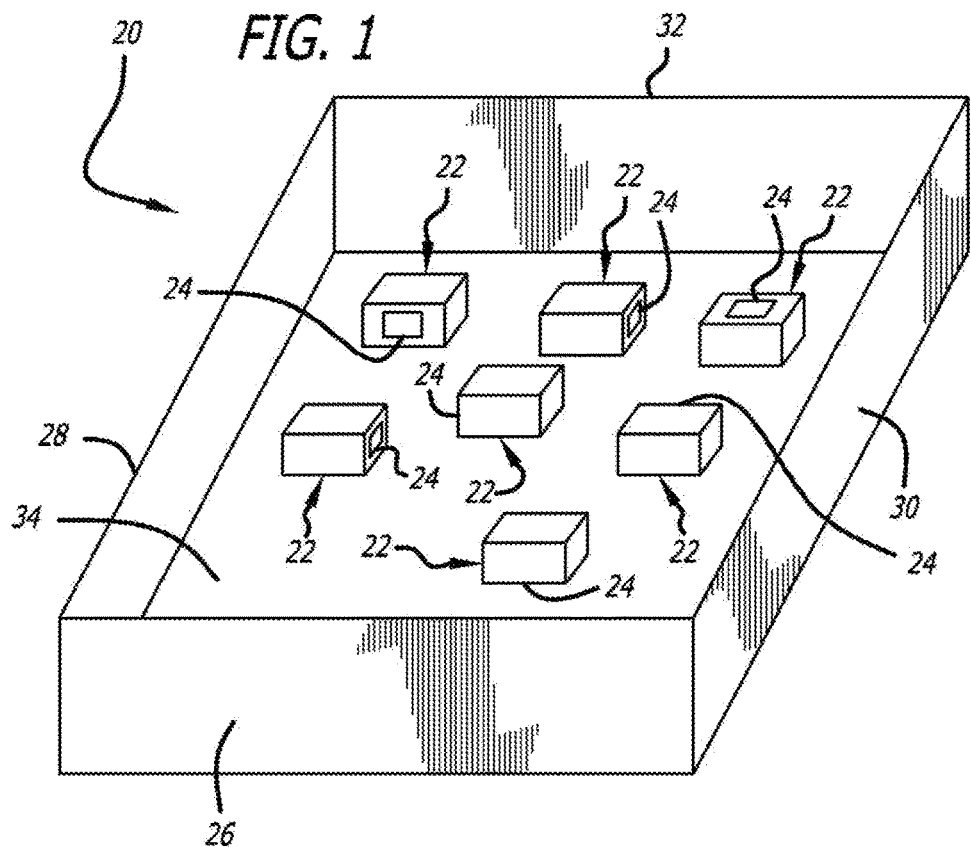
FIG. 1 is a schematic diagram of a drawer that may be positioned within a medical dispensing cabinet, showing the storage of a plurality of medical articles randomly positioned in the drawer, each of those articles having an integral RFID tag oriented randomly.

Referring now in more detail to the exemplary drawings for purposes of illustrating embodiments of the invention, wherein like reference numerals designate corresponding or like elements among the several views, there is shown in FIG. 1 a schematic representation of a partial enclosure 20 in which a plurality of medical articles 22 are stored, each with a respective RFID tag 24 that has a unique identification number. The partial enclosure may comprise a drawer having a front 26, a left side 28, a right side 30, a rear 32, and a bottom 34. These articles are randomly distributed in the drawer with the RFID tags facing in various and random directions.

As used in regard to the embodiments herein, "reader" and "interrogator" refer to a device that excites an RFID tag and that may read or write/read. The data capture device is always referred to as a reader or an interrogator regardless of whether it can only read or is also capable of writing. A reader typically contains a radio frequency module (a transmitter and a receiver, sometimes referred to as a "transceiver"), a control unit and a coupling element (such as an antenna or antennae) to the RFID tag. Additionally, many readers include an interface for forwarding data elsewhere, such as an RS-232 interface. The reader, when transmitting, has an interrogation zone within which an RFID tag will be activated. When within the interrogation zone, the RFID tag will draw its power from the electrical/magnetic field created in the interrogation zone by the reader. In a sequential RFID system (SEQ), the interrogation field is switched off at regular intervals. The RFID tag is programmed to recognize these "off" gaps and they are used by the tag to send data, such as the tag's unique identification number. In some systems, the tag's data record contains a unique serial number that is incorporated when the tag is manufactured and which cannot be changed. This number may be associated in a database with a particular article when the tag is attached to that article. Thus, determining the location of the tag will then result in determining the location of the article to which it is attached. In other systems, the RFID tag may contain more information about the article to which it is attached, such as the name or identification of the article, its expiration date, its dose, the patient name, and other information. The RFID tag may also be writable so that it can be updated.

As used in regard to the embodiments herein, "tag" is meant to refer to an RFID transponder. Such tags typically have a coupling element, such as an antenna, and an electronic microchip. The microchip includes data storage, also referred to as memory.

Figure 2:
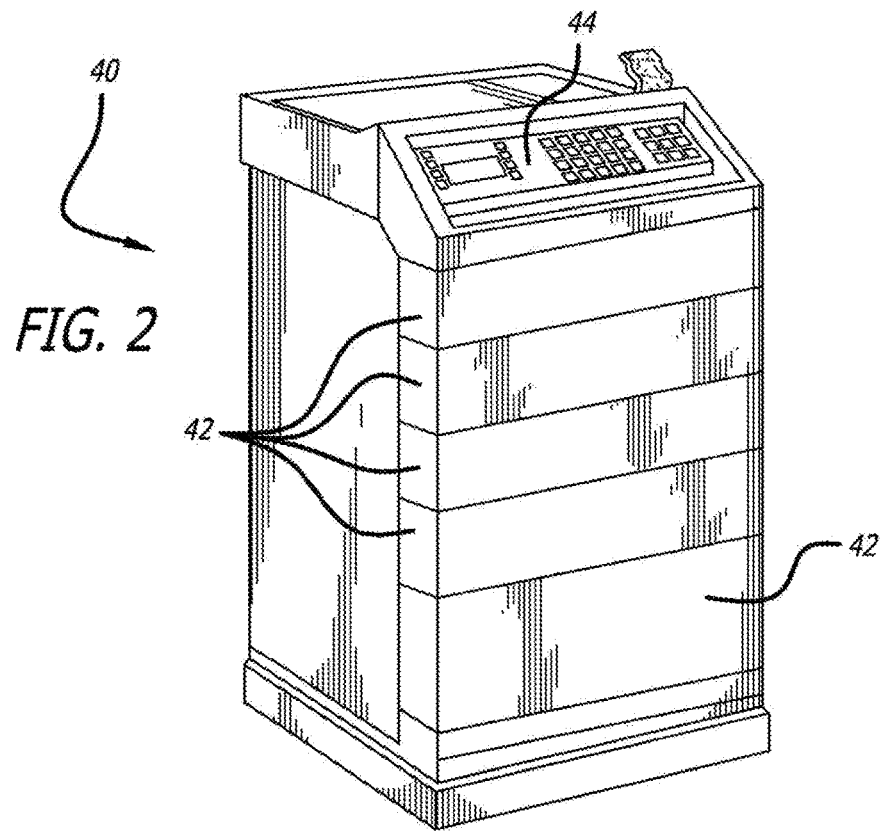
FIG. 2 is a perspective view of a medication dispensing cabinet having five drawers, one of which is similar to the schematic view of FIG. 1, the cabinet also having an integral computer for controlling access to the cabinet and performing inventory tracking by periodically reading any RFID tags placed on articles stored within the cabinet, and for reporting the identified articles to a remote computer.

FIG. 2 presents a representative medical dispensing cabinet 40 comprising a plurality of movable drawers 42. In this embodiment, there are five drawers that slide outwardly from the cabinet so that access is provided to the contents of the drawers. FIG. 1 is a schematic diagram of a representative drawer that may be positioned within the cabinet of FIG. 2 for sliding outward to provide access to the drawer's contents and for sliding inward into the cabinet to secure the drawer's contents. The cabinet also comprises an integral computer 44 that may be used to control access to the drawers and to generate data concerning access and contents, and to communicate with other systems. In this embodiment, the computer generates data concerning the number and type of articles in the drawers, the names of the patients for whom they have been prescribed, the prescribed medications and their prescribed administration dates and times, as well as other information. In a simpler system, the computer may simply receive unique identification numbers from stored articles and pass those identification numbers to an inventory control computer that has access to a database for matching the identification numbers to article descriptions.

Such a cabinet may be located at a nursing station on a particular floor of a health care institution and may contain the prescriptions for the patients of that floor. As prescriptions are prepared for the patients of that floor, they are delivered and placed into the cabinet 40. They are logged into the integral computer 44, which may notify the pharmacy of their receipt. A drawer may also contain non-prescription medical supplies or articles for dispensing to the patients as determined by the nursing staff. At the appropriate time, a nurse would access the drawer in which the medical articles are stored through the use of the computer 44, remove a particular patient's prescriptions and any needed non-prescription articles, and then close the drawer so that it is secured. In order to access the cabinet, the nurse may need to provide various information and may need a secure access code. The drawers 42 may be locked or unlocked, as conditions require.

The computer 44 in some cases may be in communication with other facilities of the institution. For example, the computer 44 may notify the pharmacy of the health care institution that a patient's prescription has been removed from the cabinet for administration at a particular day and time. The computer may also notify the finance department of the health care institution of the removal of prescriptions and other medical articles for administration to a particular patient. This medication may then be applied to the patient's account. Further, the computer 44 may communicate to administration for the purpose of updating a patient's Medication Administration Record (MAR), or e-MAR. The medication cabinet 40 computer 44 may be wirelessly connected to other computers of the health care institution or may have a wired connection. The cabinet may be mounted on wheels and may be moved about as needed or may be stationary and unable to move.

Figure 3:
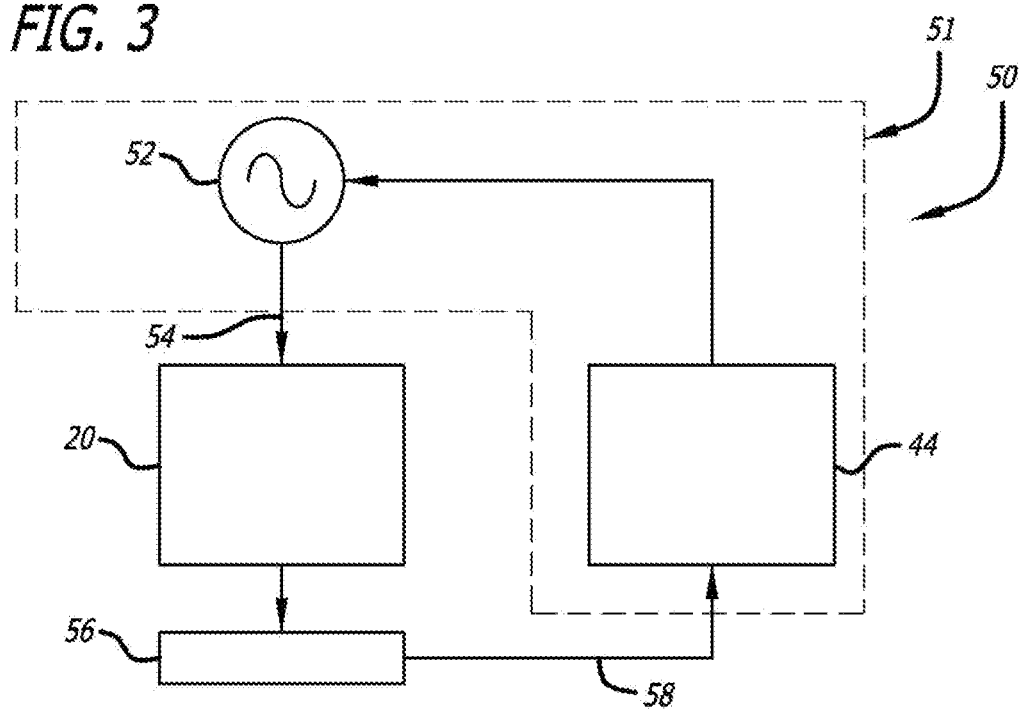
FIG. 3 is a block and flow diagram showing an embodiment in which an RFID reader transmits activating EM energy into a drawer containing RFID tags with a single transmitting antenna, receives the data output from the activated RFID tags with a single receiving antenna, a computer controlling the transmission of activating energy and receiving the data from the activated RFID tags for processing.
Figure 4:
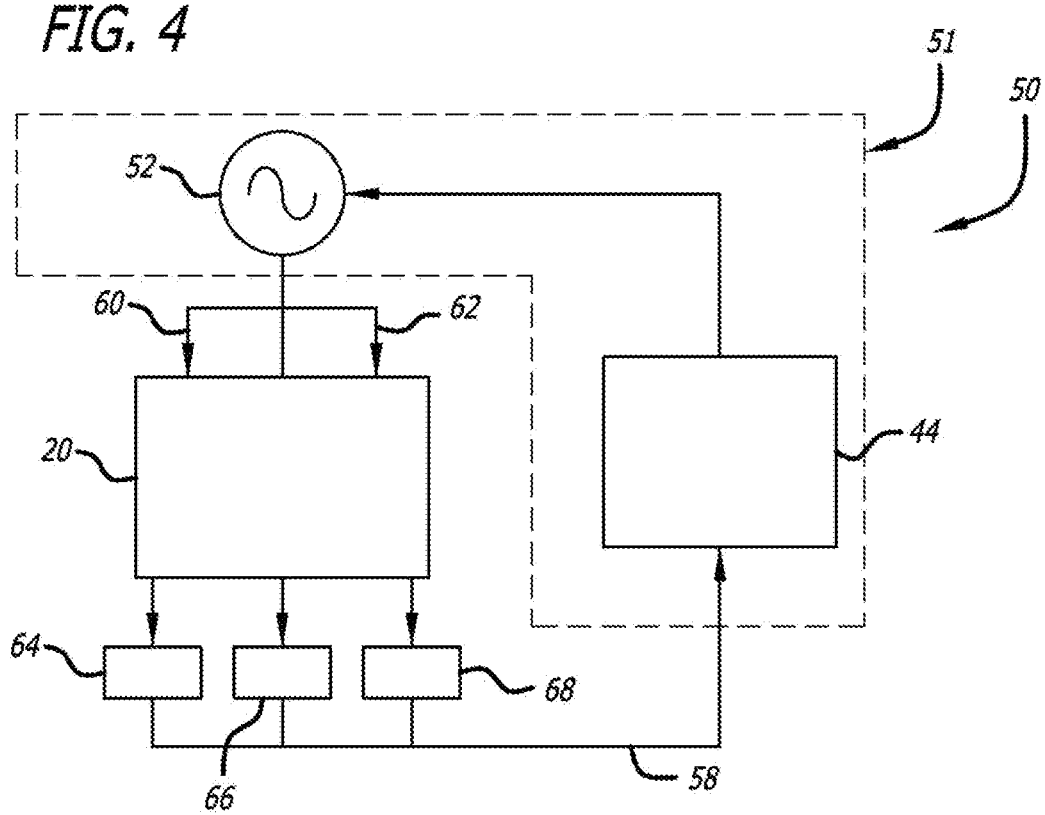
FIG. 4 is a block and flow diagram similar to FIG. 3 showing an embodiment in which an RFID reader transmits activating EM energy into a drawer containing RFID tags with two transmitting antennae, receives the data output from the activated RFID tags with three receiving antennae, and as in FIG. 3, a computer controlling the transmission of activating energy and receiving the data from the activated RFID tags for processing.

Systems that use RFID tags often employ an RFID reader in communication with one or more host computing systems that act as depositories to store, process, and share data collected by the RFID reader. Turning now to FIGS. 3 and 4, a system and method 50 for tracking articles are shown in which a drawer 20 of the cabinet 40 of FIG. 2 is monitored to obtain data from RFID tags disposed with articles in that drawer. As mentioned above, a robust field of EM energy needs to be established in the storage site so that the RFID tags mounted to the various stored articles will be activated, regardless of their orientation.

In FIGS. 3 and 4, the tracking system 50 is shown for identifying articles in an enclosure and comprises a transmitter 52 of EM energy as part of an RFID reader. The transmitter 52 has a particular frequency, such as 915 MHZ, for transmitting EM energy into a drawer 20 by means of a transmitting antenna 54. The transmitter 52 is configured to transmit the necessary RFID EM energy and any necessary timing pulses and data into the enclosure 20 in which the RFID tags are disposed. In this case, the enclosure is a drawer 20. The computer 44 of an RFID reader 51 controls the EM transmitter 52 to cycle between a transmit period and a non-transmit, or off, period. During the transmit period, the transmitted EM energy at or above a threshold intensity level surrounds the RFID tags in the drawer thereby activating them. The transmitter 52 is then switched to the off period during which the RFID tags respond with their respective stored data.

The embodiment of FIG. 3 comprises a single transmitting probe antenna 54 and a single receiving antenna 56 oriented in such a manner so as to optimally read the data transmitted by the activated RFID tags located inside the drawer 20. The single receiving antenna 56 is communicatively coupled to the computer 44 of the reader 50 located on the outside of the drawer 20 or on the inner bottom of the drawer. Other mounting locations are possible. Coaxial cables 58 or other suitable signal links can be used to couple the receiving antenna 56 to the computer 44. A wireless link may be used in a different embodiment. Although not shown in the figures, those skilled in the art will recognize that various additional circuits and devices are used to separate the digital data from the RF energy, for use by the computer. Such circuits and devices have not been shown in FIGS. 3 and 4 to avoid unneeded complexity in the drawing.

The embodiment of FIG. 4 is similar to the embodiment of FIG. 3 but instead uses two transmitting probe antennae 60 and 62 and three receiving antennae 64, 66, and 68. The configuration and the number of transmitting probe antennae and receiving antennae to be used for a system may vary based at least in part on the size of the enclosure 20, the frequency of operation, the relationship between the operation frequency and the natural resonance frequency of the enclosure, and the expected number of RFID tags to be placed in it, so that all of the RFID tags inside the enclosure can be reliably activated and read. The location and number of RFID reader components can be dependent on the particular application. For example, fewer components may be required for enclosures having a relatively small size, while additional components, such as shown in FIG. 4, may be needed for larger enclosures. Although shown in block form in FIGS. 3 and 4, it should be recognized that each receiving antenna 56, 64, 66, and 68 of the system 50 may comprise a sub-array in a different embodiment.

The transmit antennae (54, 60, and 62) and the receive antennae (56, 64, 66, and 68) may take different forms. In one embodiment as is discussed in more detail below, a plurality of "patch" or microstrip antennae were used as the reader receiving antennae and were located at positions adjacent various portions of the bottom of the drawer while the transmit antennae were wire probes located at positions adjacent portions of the top of the drawer. It should be noted that in the embodiments of FIGS. 3 and 4, the RFID reader 50 may be permanently mounted in the same cabinet at a strategic position in relation to the drawer 20. In another form, a transmitting antenna is a probe that injects electromagnetic energy into the enclosure. This same probe is further configured to receive identification data provided by identification devices of the medical storage container and the medical articles stored in the medical storage container when they are located in the enclosure.

One solution for reliably interrogating densely packed or randomly oriented RFID tags in an enclosure is to treat the enclosure as a resonant cavity. Establishing a resonance within the cavity enclosure can result in a robust electromagnetic field capable of activating all RFID tags in the enclosure. This can be performed by building an enclosure out of electrically conductive walls and exciting the metallic enclosure, or cavity, using a probe or probes to excite transverse electric (TE) or transverse magnetic (TM) fields in the cavity at the natural frequency of resonance of the cavity. This technique will work if the cavity dimensions can be specifically chosen to set up the resonance at the frequency of operation or if the frequency of operation can be chosen for the specific enclosure size. Since there are limited frequency bands available for use in RFID applications, varying the RFID frequency is not an option for many applications. Conversely, requiring a specific set of physical dimensions for the enclosure so that the natural resonant frequency of the enclosure will equal the available RFID tag activating frequency will restrict the use of this technique for applications where the enclosure needs to be of a specific size. This latter approach is not practical in view of the many different sizes, shapes, and quantities of medical articles that must be stored.

Referring now to FIG. 5, a rectangular enclosure 80 is provided that may be formed as part of a medical cabinet, such as the cabinet shown in FIG. 2. It may be embodied as a frame disposed about a non-metallic drawer in such a cabinet. The enclosure 80 is formed of metallic or metallized walls 82, floor 83, and ceiling 84 surfaces, all of which are electrically conductive. All of the walls 82, floor 83, and ceiling 84 may also be referred to herein as "walls" of the enclosure. FIG. 5 also shows the use of an energy coupling or probe 86 located at the top surface 84 of the enclosure 80. In this embodiment, the probe takes the form of a capacitor probe 88 in that the probe 88 has a first portion 94 that proceeds axially through a hole 90 in the ceiling 84 of the enclosure. The purpose of the coupling is to efficiently transfer the energy from the source 52 (see FIGS. 3 and 4) to the interior 96 of the enclosure 80. The size and the position of the probe are selected for effective coupling and the probe is placed in a region of maximum field intensity. In FIG. 5, a $TE_{01}$ mode is established through the use of capacitive coupling. The length and distance of the bent portion 94 of the probe 88 affects the potential difference between the probe and the enclosure 80.

Similarly, FIG. 6 presents an inductive coupling 110 of the external energy to an enclosure 112. The coupling takes the form of a loop probe 114 mounted through a side wall 116 of the enclosure. The purpose of this probe is to establish a $TM_{01}$ mode in the enclosure.

Figure 7:
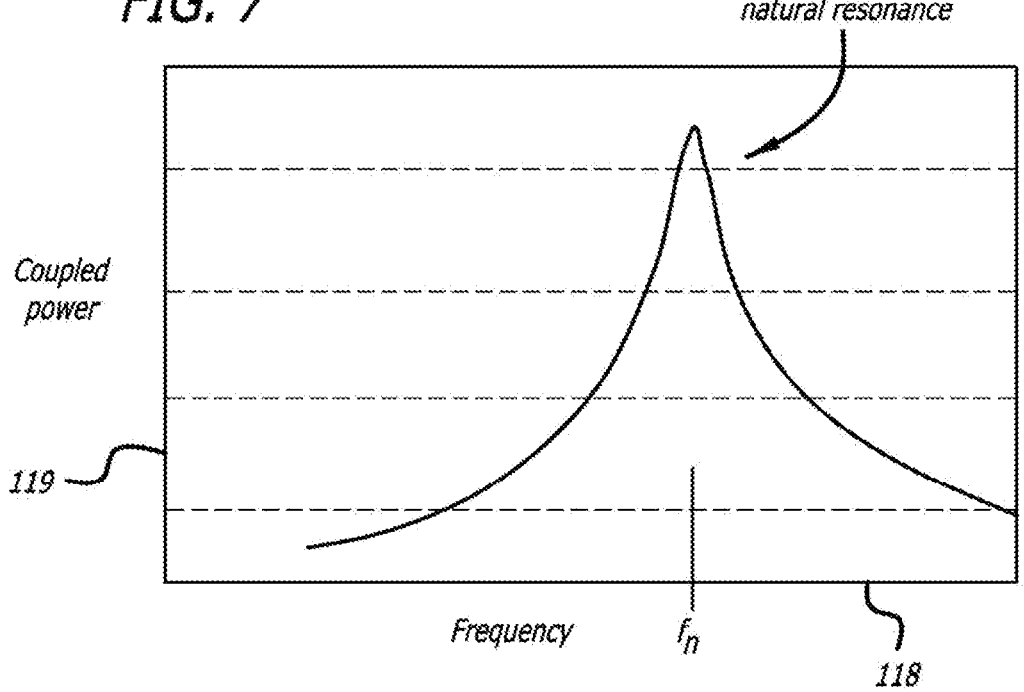
FIG. 7 shows a plot of coupled power in an enclosure as a function of frequency for a resonant enclosure where $F_n$ is the natural resonance frequency of the enclosure.

The rectangular enclosures 80 and 112 shown in FIGS. 5 and 6 each have a natural frequency of resonance $f_n$, shown in FIG. 7 and indicated on the abscissa axis 118 of the graph by $f_n$. This is the frequency at which the coupled power in the enclosure is the highest, as shown on the ordinate axis 119 of the graph. If the injected energy to the enclosure does not match the $f_n$ frequency, the coupled power will not benefit from the resonance phenomenon of the enclosure. In cases where the frequency of operation cannot be changed, and is other than $f_n$, and the size of the enclosure cannot be changed to obtain an $f_n$ that is equal to the operating frequency, another power coupling apparatus and method must be used. In accordance with aspects of the invention, an apparatus and method are provided to result in a forced resonance $f_f$ within the enclosure to obtain a standing wave within the enclosure with constructive interference. Such a standing wave will establish a robust energy field within the enclosure strong enough to activate all RFID tags residing therein.

Figure 8:
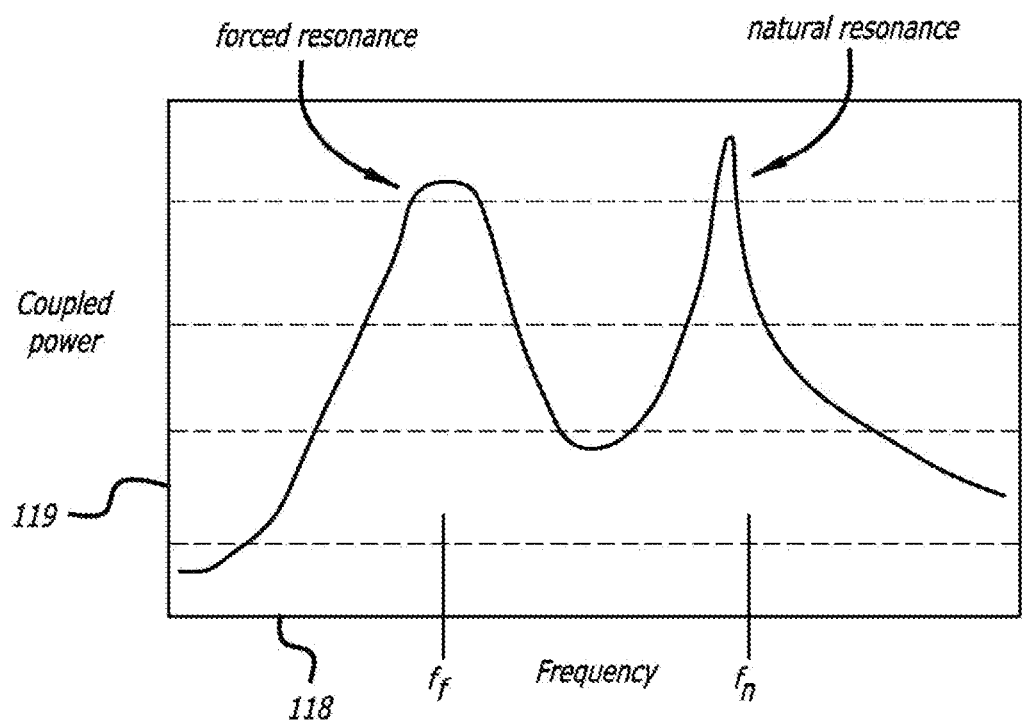
FIG. 8 shows a plot of coupled power (ordinate axis) in an enclosure as a function of frequency (abscissa axis), where $f_f$ is a forced resonance frequency, or otherwise referred to as a frequency that is not equal to the resonant frequency of the enclosure, and $f_n$ is the natural resonant frequency of the enclosure, showing the establishment of a robust field of coupled power in the enclosure at the $f_f$ frequency.

When an EM wave that is resonant with the enclosure enters, it bounces back and forth within the enclosure with low loss. As more wave energy enters the enclosure, it combines with and reinforces the standing wave, increasing its intensity (constructive interference). Resonation occurs at a specific frequency because the dimensions of the cavity are an integral multiple of the wavelength at the resonance frequency. In the present case where the injected energy is not at the natural resonance frequency $f_n$ of the enclosure, a solution in accordance with aspects of the invention is to set up a "forced resonance" in an enclosure. This forced resonance is different from the natural resonance of the enclosure in that the physical dimensions of the enclosure are not equal to an integral multiple of the wavelength of the excitation energy, as is the case with a resonant cavity. A forced resonance can be achieved by determining a probe position, along with the probe length to allow for energy to be injected into the cavity such that constructive interference results and a standing wave is established. The energy injected into the enclosure in this case will set up an oscillatory field region within the cavity, but will be different from a standing wave that would be present at the natural resonance frequency $f_n$ of a resonant cavity. The EM field excited from this forced resonance will be different than the field structure found at the natural resonance of a resonant cavity, but with proper probe placement of a probe, a robust EM field can nevertheless be established in an enclosure for RFID tag interrogation. Such is shown in FIG. 8 where it will be noted that the curve for the forced resonance $f_f$ coupled power is close to that of the natural resonance $f_n$.

Turning now to FIG. 9, an enclosure 120 having two energy injection probes is provided. The first probe 86 is capacitively coupled to the enclosure 120 in accordance with FIG. 5 to establish a $TE_{01}$ mode. The second probe 114 is inductively coupled to the enclosure 120 in accordance with FIG. 6 to establish a $TM_{01}$ mode. These two probes are both coupled to the enclosure to inject energy at a frequency $f_f$ that is other than the natural resonance frequency $f_n$ of the enclosure. The placement of these probes in relation to the ceiling 126 and walls 128 of the enclosure will result in a forced resonance within the enclosure 120 that optimally couples the energy to the enclosure and establishes a robust EM field within the enclosure for reading RFID tags that may be located therein. The placement of these probes in relation to the walls of the enclosure, in accordance with aspects of the invention, result in the forced resonance curve $f_f$ shown in FIG. 8.

Figure 11:
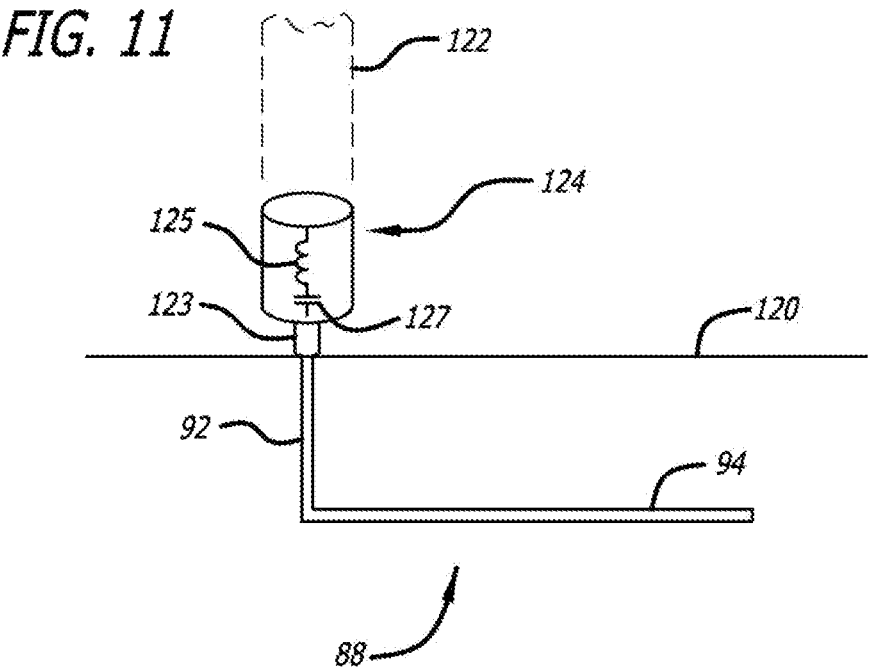
FIG. 11 shows a probe, a connector, and a passive matching circuit that is used to improve the impedance match between the probe and enclosure.

Referring briefly to FIG. 10, an impedance matching circuit 121 is shown that functions to match the impedance of a source of energy 122 to the enclosure 120. The impedance matching circuit is located between the coaxial cable 122 that feeds activating energy to the enclosure 120 and the capacitively coupled probe 88 through a hole in the metallic ceiling 126 of the enclosure. While the hole is not shown in the drawing of FIG. 10, the insulator 123 that electrically insulates the probe from the metallic ceiling is shown. In this case, the matching circuit 121 consists of only a resistive attenuator 124 used to reduce reflections of energy by the enclosure 120. However, as will be appreciated by those of skill in the art, capacitive and inductive components are likely to exist in the enclosure and in the coupling 88. FIG. 11 on the other hand presents an impedance matching circuit 124 having passive reactive components for use in matching the impedance of the coaxial cable/energy source 122 and the enclosure 120. In this exemplary impedance matching circuit 124, an inductive component 125 and a capacitive component 127 are connected in series, although other configurations, including the addition of a resistive component and other connection configurations, are possible.

Passive components such as resistors, inductors, and capacitors shown in FIGS. 10 and 11 can be used to form matching circuits to match the impedances of the energy source and the enclosure. This will aid in coupling power into the enclosure. However, the passive matching circuit will improve the impedance match for a specific enclosure loading, such as an empty enclosure, partially loaded, or fully loaded enclosure. But as the enclosure contents are varied, the impedance match may not be optimized due to the variation in contents in the enclosure causing the impedance properties of the enclosure to change.

Figure 12:
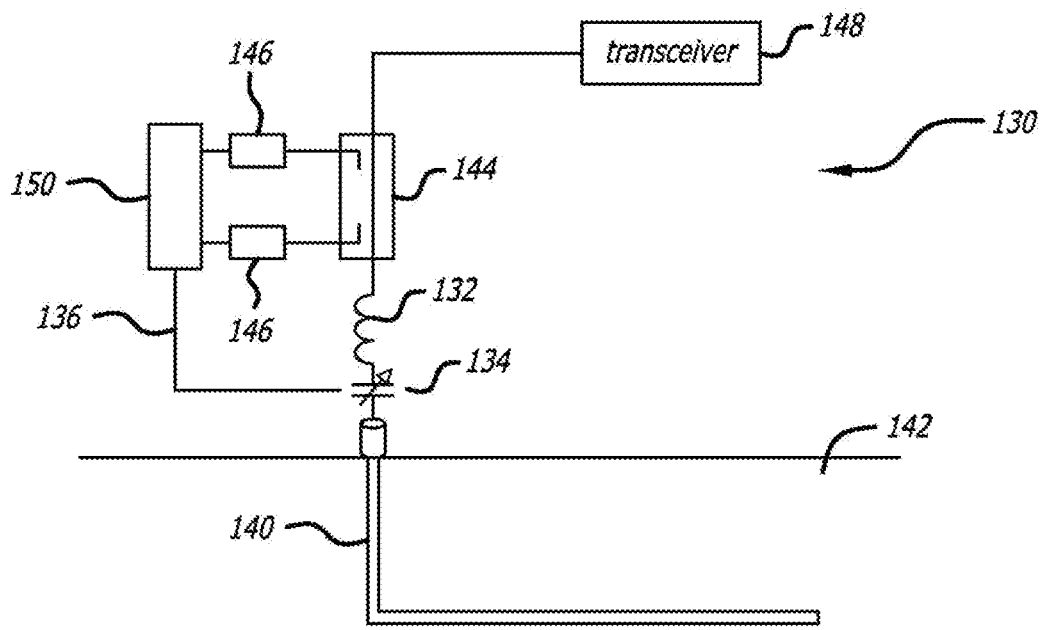
FIG. 12 shows an active matching circuit connected between a probe located in an enclosure and a transceiver, the active matching circuit comprising a tunable capacitor, a dual-directional coupler, multiple power sensors, and a comparator used to provide a closed-loop, variable matching circuit to improve the impedance match between the probe and the enclosure.

This non-optimal impedance match caused by variation in enclosure loading can be overcome by the use of an active impedance matching circuit which utilizes a closed loop sensing circuit to monitor forward and reflected power. Referring now to FIG. 12, an active matching circuit 130 is provided that comprises one or several fixed value passive components such as inductors 132, capacitors 134, or resistors (not shown). In addition, one or several variable reactance devices, such as a tunable capacitor 134, are incorporated into the circuit; these tunable devices making this an active impedance matching circuit. The tunable capacitor 134 can take the form of a varactor diode, switched capacitor assembly, MEMS capacitor, or BST (Barium Strontium Titanate) capacitor. A control voltage is applied to the tunable capacitor 134 and varied to vary the capacitance provide by the device. The tunable capacitor 134 provides the capability to actively change the impedance match between the probe 140 and the enclosure 142.

To complete the active matching circuit, a dual directional coupler 144 along with two power sensors 146 can be incorporated. The dual directional coupler 144 and the power sensors 146 provide the ability to sense forward and reflected power between the RFID transceiver 148 and the active matching circuit 130 and enclosure 142. Continuous monitoring of the ratio of forward and reflected power by a comparator 150 provides a metric to use to adjust the tunable capacitor 134 to keep the probe 140 impedance matched to the enclosure 142. An ability to continuously monitor and improve the impedance match as the contents of the enclosure are varied is provided with the active matching circuit 130.

Figure 13:
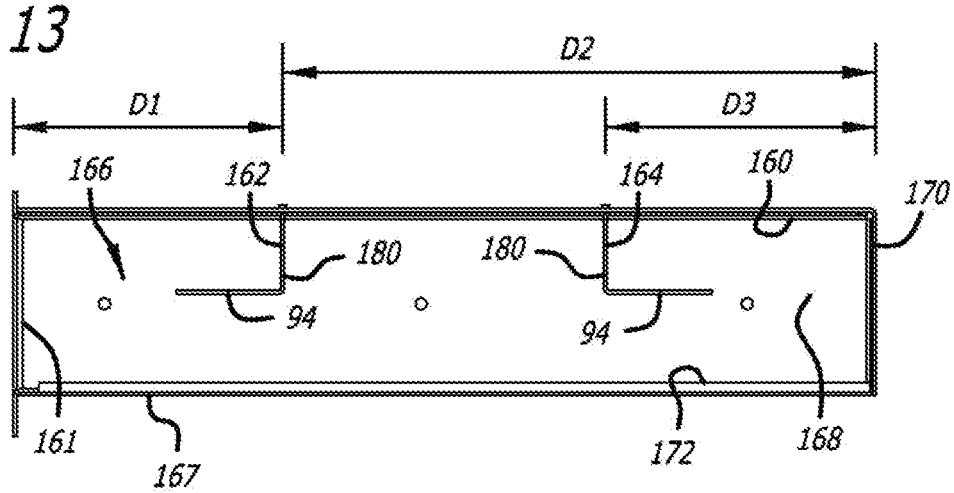
FIG. 13 provides a side cross-sectional view of the cabinet of FIG. 2 at the location of a drawer with the drawer removed for clarity, showing the placement of two probe antennae in a "ceiling mount" configuration for establishing a robust EM field in the drawer when it is in place in the cabinet in the closed position.

Referring now to the side cross-sectional view of FIG. 13, two ceiling-mounted 160 probe antennae 162 and 164 are shown mounted within an enclosure, which may also be referred to herein as a cavity 166, which in this embodiment, operates as a Faraday cage. As shown, the Faraday cage 166 comprises walls (one of which is shown) 168, a back 170, a floor 172, a ceiling 160, and a front 161 (only the position of the front wall is shown). All surfaces forming the cavity are electrically conductive, are electrically connected with one another, and are structurally formed to be able to conduct the frequency of energy $f_f$ injected by the two probes 162 and 164. In this embodiment, the cavity 166 is constructed as a metal frame 167 that may form a part of a medical supply cabinet similar to that shown in FIG. 2. Into that metal frame may be mounted a slidable drawer. The slidable drawer in this embodiment is formed of electrically inert material, that is, it is not electrically conductive, except for the front. When the drawer is slid into the cabinet to a closed configuration, the electrically conductive front panel of the drawer comes into electrical contact with another part or parts of the metallic frame 167 thereby forming the front wall 161 of the Faraday cage 167.

The amount of penetration or retention into the cavity by the central conductor 180 of each probe is selected so as to achieve optimum coupling. The length of the bent portion 94 of the probe is selected to result in better impedance matching. The position of the probe in relation to the walls of the cavity is selected to create a standing wave in the cavity. In this embodiment, the probe antennae 162 and 164 have been located at a particular distance D1 and D3 from respective front 161 and back 170 walls. These probe antennae, in accordance with one aspect of the invention, are only activated sequentially after the other probe has become inactivated. It has been found that this configuration results in a standing wave where the injected energy waves are in phase so that constructive interference results.

Figure 14:
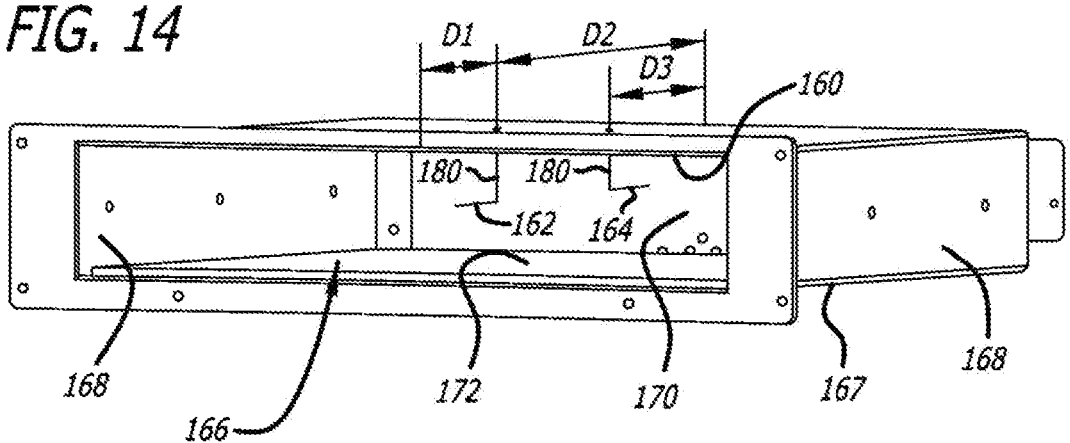
FIG. 14 is a perspective view of the metallic enclosure showing the probe configuration of FIG. 13 again showing the two probe antennae for establishing a robust EM field in a drawer to be inserted.

FIG. 14 is a front perspective view of the probe configuration of FIG. 13 again showing the two probe antennae 162 and 164 located in a Faraday-type enclosure 166 for establishing a robust EM field in an article storage drawer to be inserted. It should be noted again that the Faraday cavity 166 is constructed as a metallic frame 167. In this figure, the cavity is incomplete in that the front surface of the "cage" is missing. In one embodiment, this front surface is provided by an electrically conductive front panel of a slidable drawer. When the drawer is slid into the cabinet, the front panel will make electrical contact with the other portions of the metallic frame 167 thereby completing the Faraday cage 166, although other portions of the drawer are plastic or are otherwise non-electrically conductive. In the embodiment discussed and shown herein, the two probe antennae 162 and 164 are both located along a centerline between the side walls 166 and 168 of the frame 166. The enclosure in one embodiment was 19.2 inches wide with the probe antennae spaced 9.6 inches from each side wall. This centered location between the two side walls was for convenience in the case of one embodiment. The probes may be placed elsewhere in another embodiment. In this embodiment, the spacing of the probes 162 and 164 from each other is of little significance since they are sequentially activated. Although not shown, two receiving antennae will also be placed into the Faraday cage 166 to receive response signals from the activated RFID tags residing within the cavity 166.

It will also be noted from reference to the figures that the probes each have a bent portion used for capacitive coupling with the ceiling 160 of the cavity, as is shown in FIG. 13. The front probe 162 is bent forward while the back probe 164 is bent rearward A purpose for this configuration was to obtain more spatial diversity and obtain better coverage by the EM field established in the drawer. Other arrangements may be possible to achieve a robust field within the cavity 166. Additionally two probes were used in the particular enclosure 166 so that better EM field coverage of the enclosure 166 would result.

Figure 15:
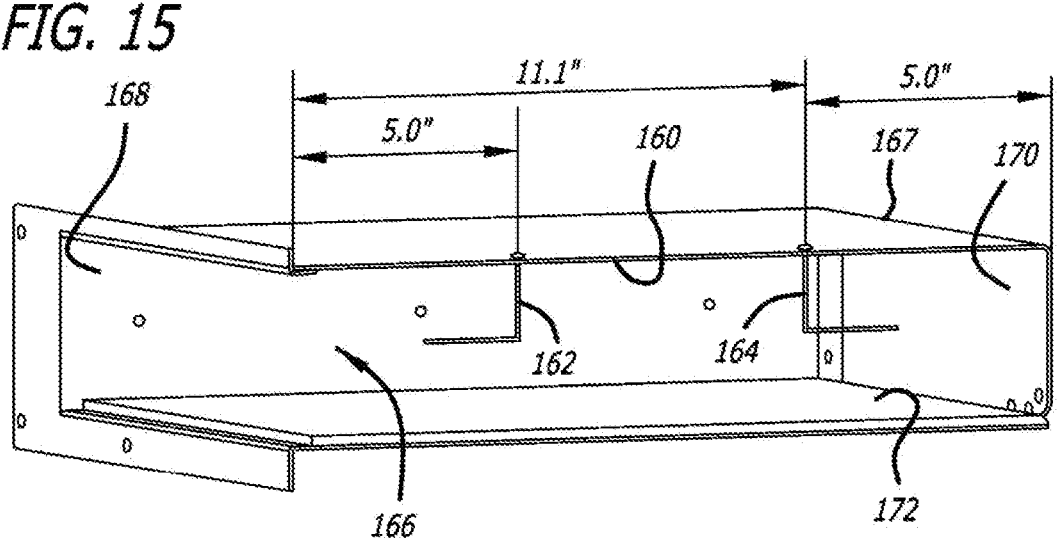
FIG. 15 is a cutaway perspective side view of the metallic enclosure or frame in which are mounted the dual probe antennae of FIGS. 13 and 14 with the drawer removed for clarity.

FIG. 15 is a cutaway perspective side view of the dual probe antennae 162 and 164 of FIGS. 13 and 14, also with the drawer removed for clarity. The front probe 162 is spaced from the left side wall by ½ λ of the operating frequency Fr as shown. It will be noted that the probes each have a bent portion used for capacitive coupling with the ceiling 160 of the enclosure 166 as shown in FIG. 13. The front probe 162 is bent forward for coupling with the more forward portion of the enclosure while the back probe 164 is bent rearward for coupling with the more rearward portion of the enclosure 166 to obtain more spatial diversity and obtain better coverage by the EM field in the drawer. Other arrangements may be possible to achieve a robust field and further spatial diversity and coverage within the enclosure.

Figure 16:
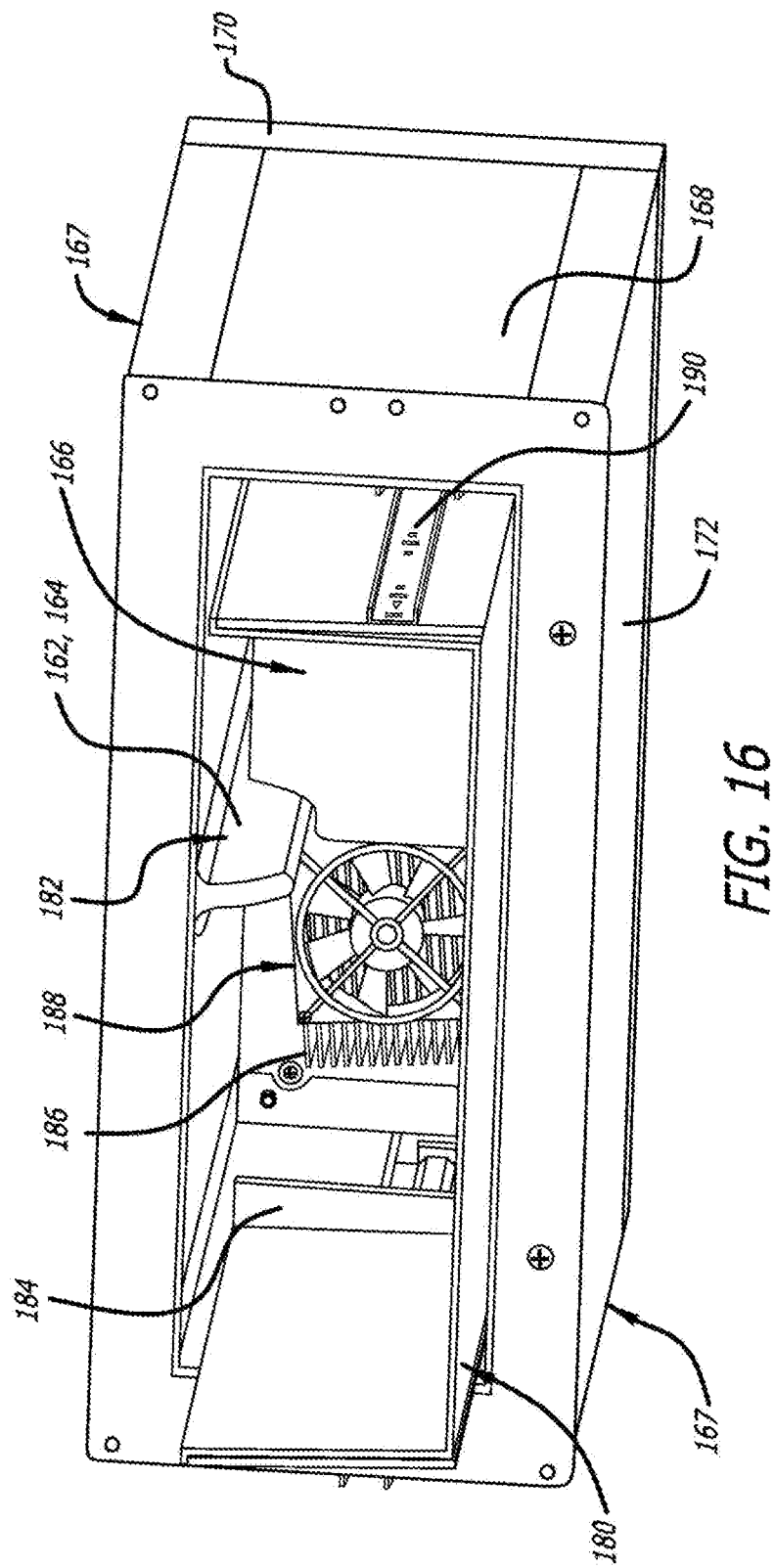
FIG. 16 is a frontal perspective view of the view of FIG. 14 with a cutaway plastic drawer in place in the metallic enclosure and further showing the dual ceiling mount probe antennae protected by an electromagnetically inert protective cover, and further showing cooling system components mounted at the back of the cabinet near the drawer's back, the drawing also showing a partial view of a drawer slide mechanism for ease in sliding the drawer between open and closed positions in the cabinet, the drawer front and rear panels having been cutaway in this view.

FIG. 16 is a frontal upward-looking perspective view of the frame 167 forming a Faraday cage 166 showing a portion of a drawer 180 that has been slidably mounted within the frame 167. The front metallic panel of the drawer has been removed so that its sliding operation can be more clearly seen. It will also be noted that the dual ceiling mount probe antennae 162 and 164 have been covered and protected by an electromagnetically inert protective cover 182. The drawer is formed of a non-metallic material, such as a plastic or other electromagnetic inert material having a low RF constant. The back 184 of the drawer has also been cut away so that a cooling system comprising coils 186 and a fan 188 located in the back of the frame 167 can be seen. In this case, the drawer 180 is slidably mounted to the Faraday cage frame with metallic sliding hardware 190. The sliding hardware of the drawer is so near the side of the frame 167 of the enclosure 166 and may be in electrical contact with the metallic slide hardware of the side walls 168 of the enclosure that these metallic rails will have only a small effect on the EM field established within the enclosure.

Figure 17:
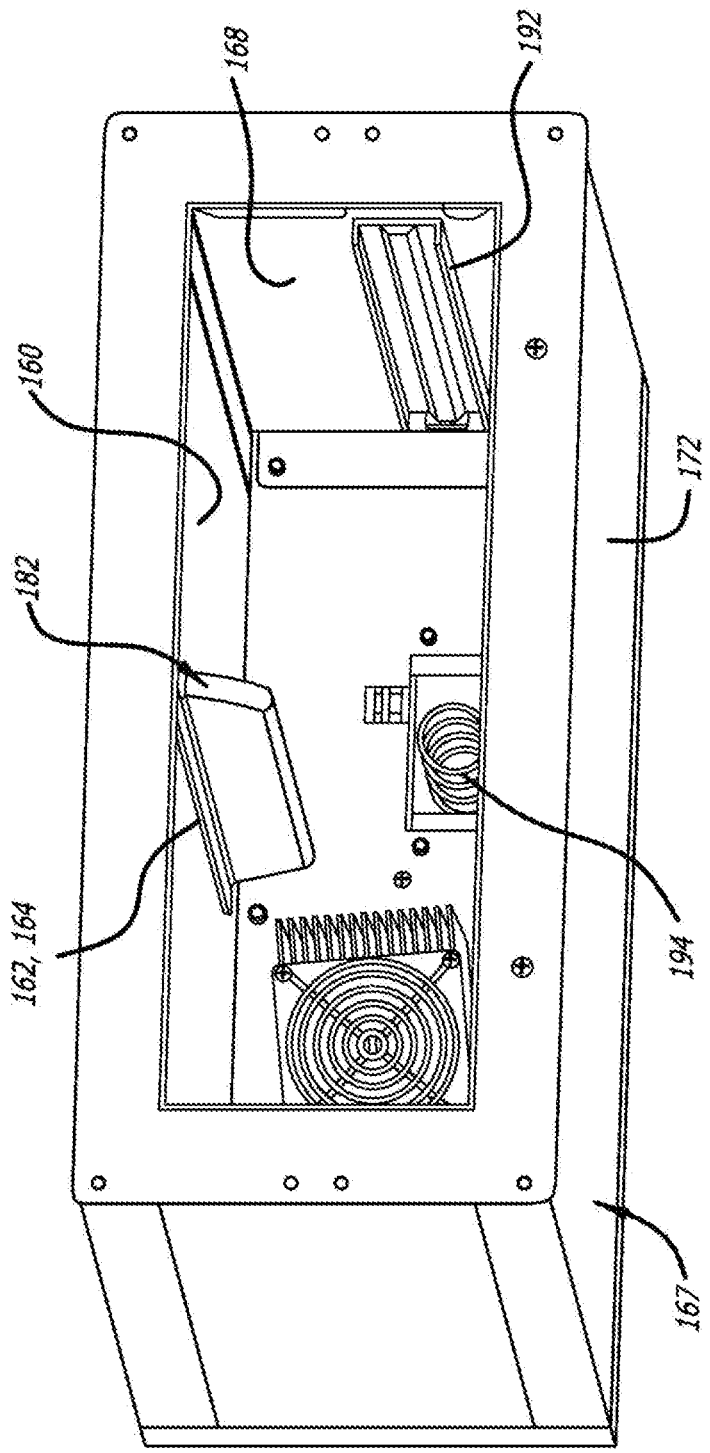
FIG. 17 is a frontal perspective view at the opposite angle from that of FIG. 16 with the plastic drawer completely removed showing the dual ceiling mount probe antennae protected by the EM inert protective cover mounted to the metallic enclosure, and further showing the cooling system components of FIG. 16 mounted at the back of the cabinet as a spring loading feature to automatically push the drawer to the open position when the drawer's latch is released, the figure also showing a mounting rail for receiving the slid of the drawer.

FIG. 17 is an upward looking, frontal perspective view at the opposite angle from that of FIG. 16; however, the drawer has been removed. The frame 167 in this embodiment includes a mounting rail 192 for receiving the slide of the drawer 180. In this embodiment, the mounting rail is formed of a metallic material; however, it is firmly attached to a side 168 of the Faraday cage and thus is in electrical continuity with the cage. The figure also shows a spring mechanism 194 used to assist in sliding the drawer outward so that access to the articles stored in the drawer may be gained. The spring is configured to push automatically the drawer outward when the drawer's latch is released.

Figure 18:
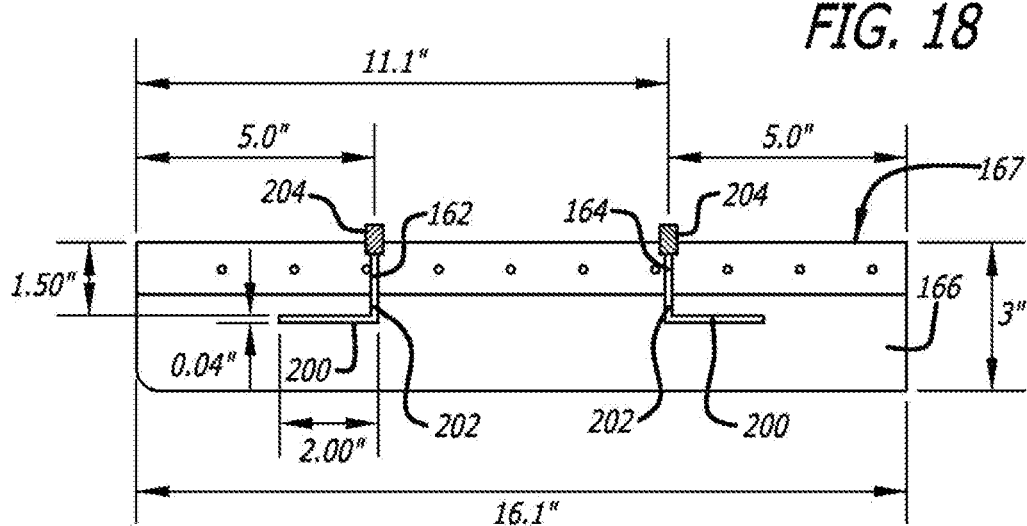
FIG. 18 is a schematic view with measurements in inches of the placement of two $TE_{01}$ mode probes in the top surface of the enclosure shown in FIGS. 13-15.

FIG. 18 is a schematic view showing measurements of the placement of two $TE_{01}$ mode capacitive coupling probes 162 and 164 in the ceiling 160 of the frame 167 shown in FIGS. 13-15. In this embodiment, the frequency of operation with the RFID tags is 915 MHZ, which therefore has a wavelength of 0.32764 meters or 1.07494 feet. One-half wavelength is therefore 0.16382 meters or 6.4495 inches. The length of the capacitive coupling bent portion 200 of each of the probes is 5.08 cm or 2.00 in. The length of the axial extension 202 of the probes into the enclosure is 3.81 cm or 1.50 in., as measured from the insulator 204 into the enclosure 166. The probe configuration and placement in the embodiment was based on an operation frequency of 915 MHz. In one embodiment, the enclosure 166 had a depth of 16.1 inches (40.89 cm), a width of 19.2 inches (48.77 cm), and a height of 3 inches (7.62 cm). It was found that the optimum probe placements for this size and shape (rectangular) enclosure and for the 915 MHz operating frequency were: the front probe was spaced from the front wall by 5.0 inches (12.7 cm) and the rear probe was spaced from the back wall by 5.0 inches (12.7 cm). As discuss above, the probes in this embodiment would only be activated sequentially.

Figure 19:
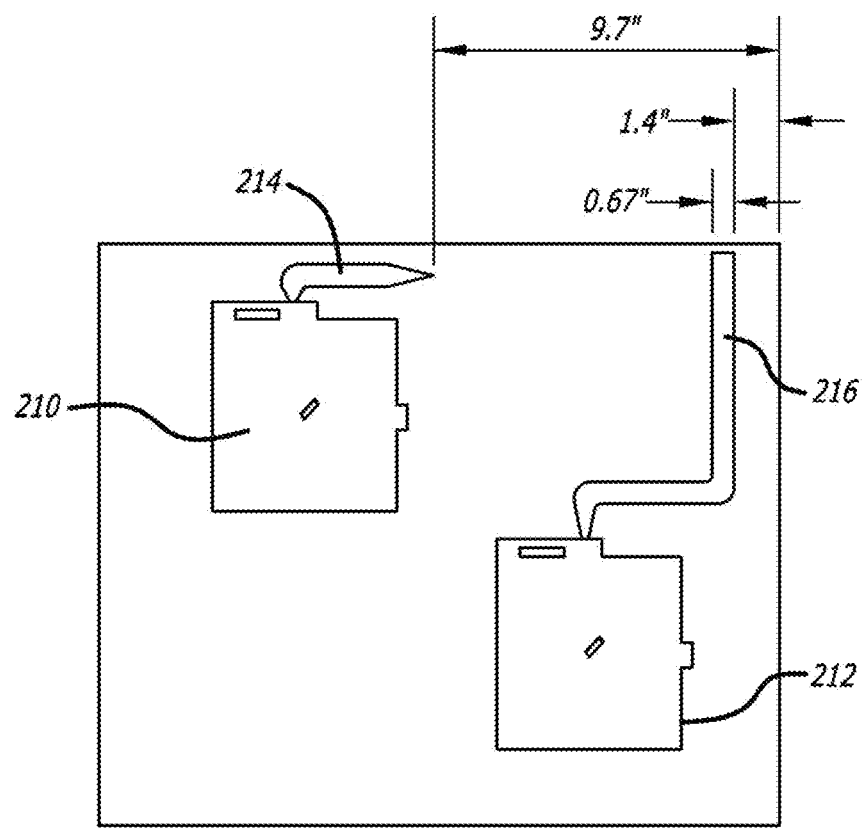
FIG. 19 is a schematic view of the size and placement within the drawer of FIG. 16 of two microstrip or "patch" antennae and their microstrip conductors disposed between respective antennae and the back of the drawer at which they will be connected to SMA connectors in one embodiment, for interconnection with other components.

FIG. 19 is a schematic view of the size and placement within the enclosure 166 of FIG. 16 of two microstrip or "patch" antennae 210 and 212 and their microstrip conductors 214 and 216 disposed between the respective antennae and the back of the enclosure at which they will be connected to SMA connectors (not shown) in one embodiment. Feed lines 58 (FIG. 3) may be connected to those SMA connectors and routed to the computer 44 for use in communicating the RFID signals for further processing. The measurements of the spacing of some of the microstrip components are provided in inches. The spacing of 9.7 in. is equivalent to 24.64 cm. The width of the microstrip line of 0.67 in. is equivalent to 17.0 mm. The spacing of 1.4 in. is equivalent to 3.56 cm. Other configurations and types of receiving antennae may be used, as well as different numbers of such antennae. In the present embodiment, the receiving antennae are mounted on insulation at the bottom inside surface of the metallic enclosure frame 167 so that the receiving patch antennae are not in contact with the metal surfaces of the Faraday cage.

Figure 20:
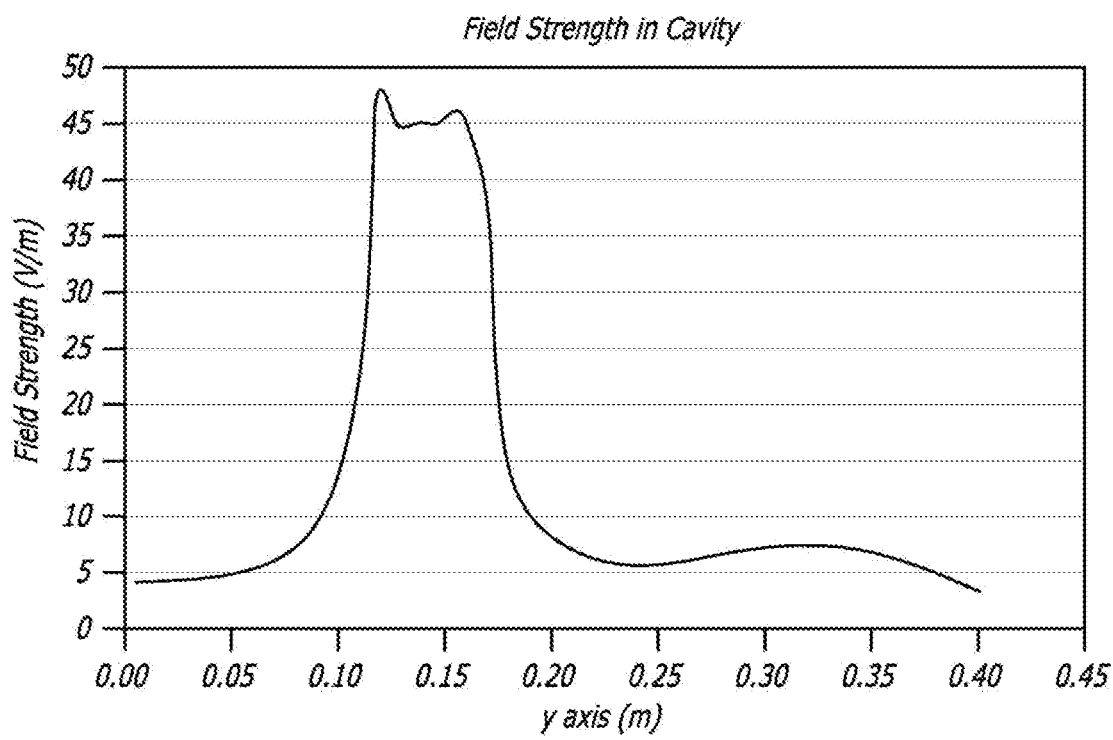
FIG. 20 is diagram of field strength in an embodiment of an enclosure with a probe placed in the enclosure at a position in accordance with the diagram of FIG. 19.
Figure 21:
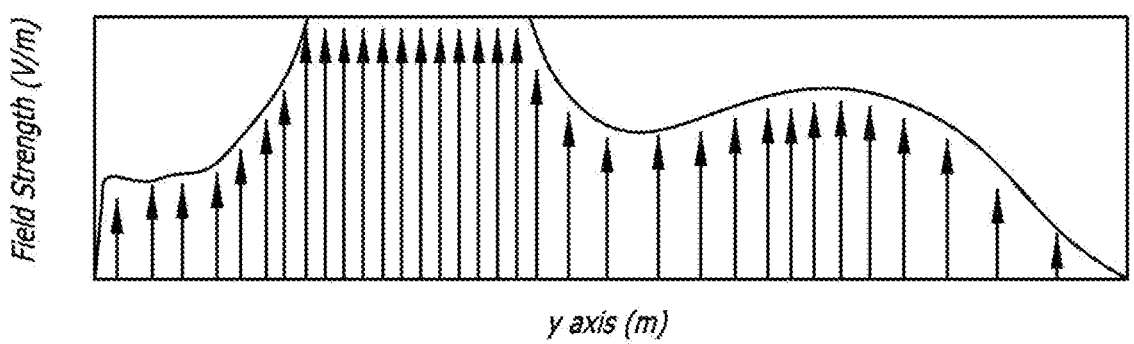
FIG. 21 is a lower scale drawing of the field intensity diagram of FIG. 20 showing a clearer view of the field intensity nearer the front and back walls of the enclosure.

Referring now to FIG. 20, the field intensity or field strength in the enclosure discussed above is shown with the ordinate axis shown in volts/meter and the abscissa axis shown in meters. It will be seen from the diagram that the maximum field intensity occurs at about 5.0 inches (0.127 m) which results from the probe positioned at 5.0 inches (12.7 cm) from the front wall and at a 915 MHz operating frequency. Referring now to FIG. 21, the scale has been reduced although the large rise in field intensity can be seen at 5.0 inches. It can also be more clearly seen that the field intensity falls off at the right wall but remains strong very close to the left wall. Therefore in an embodiment, a second probe was used that was placed 5.0 inches (12.7 cm) from the right wall thereby resulting in a mirror image field intensity to that shown in FIG. 21. The two probes 162 and 164 are activated sequentially and are not both activated simultaneously. It will be noted that better EM field coverage of the enclosure 166 is obtained with the two probes and that RFID tags on articles positioned close to the front wall 161 will be activated by the front probe 162 and that RFID tags on articles positioned close to the rear wall 170 will be activated by the rear probe 164 (see FIG. 13).

Although not intending to be bound by theory, in deriving the probe location for TE modes in a square or rectangular non-resonant cavity, the following equation can be useful:

$$N = 2 \times \frac{L_2 - L_1}{\lambda_g}$$

where: N=positive non-zero integer, for example 1, 2, 3, etc.
$L_1$=distance between probe and back wall
$L_2$=distance between probe and front wall
$\lambda_g$=wavelength in the cavity $L_1$ cannot be zero for TE modes, which implies that the probe for TE mode excitation cannot be at the front or back wall. For TM modes, the equation is the same, but N can equal zero as well as other positive integers. The probe position cannot be $\lambda_g/2$ from the front or back wall. An $L_1$ and an $L_2$ are chosen such that N can be a positive integer that satisfies the equation. For example, for the enclosure 166 discussed above:

$L_1$=4.785 inches
$L_2$=11.225 inches
$\lambda_g$=12.83 inches

Therefore, $$N = 2 \times \frac{11.215 - 4.785}{12.83} = 1.0$$

The actual enclosure had the probe located at a slightly different location (5.0 inches) than that indicated by the equation (4.785 inches) which was possibly due to the insertion of a plastic drawer in the cavity, which introduces a change in the phase from the reflected signals. The equation above is set up such that the reflected phase from both front and back walls is equal, i.e., they are "in phase" at the probe location.

The wavelength in the enclosure, $\lambda_g$, can be calculated using waveguide equations. Equations for a rectangular cavity are shown below. The cutoff frequency is required for this calculation. The equations will change for a cylindrical cavity or for other shapes.

The cutoff frequency is at the point where g vanishes. Therefore, the cutoff frequency in Hertz is:

$$(f_c)_{mn} = \frac{1}{2\pi\sqrt{\mu\varepsilon}} \sqrt{\left(\frac{m\pi}{a}\right)^2 + \left(\frac{n\pi}{b}\right)^2} \text{ (Hz)}$$

The cutoff wavelength in meters is:

$$(\lambda_c)_{mn} = \frac{2}{\sqrt{\left(\frac{m}{a}\right)^2 + \left(\frac{n}{b}\right)^2}} \text{ (m)}$$

where: a=inside width
b=inside height
m=number of ½-wavelength variations of fields in the "a" direction
n=number of ½-wavelength variations of fields in the "b" direction
ε=permittivity
μ=permeability The mode with the lowest cutoff frequency is called the dominant mode. Since $TE_{10}$ mode is the minimum possible mode that gives nonzero field expressions for rectangular waveguides, it is the dominant mode of a rectangular waveguide with a>b and so the dominant frequency is:

$$(f_c)_{10} = \frac{1}{2a\sqrt{\mu\varepsilon}} \text{ (Hz)}$$

The wave impedance is defined as the ratio of the transverse electric and magnetic fields. Therefore, impedance is:

$$Z_{TE} = \frac{E_x}{H_y} = \frac{jw\mu}{\gamma} = \frac{jw\mu}{j\beta} \Rightarrow Z_{TE} = \frac{k\eta}{\beta}$$

The guide wavelength is defined as the distance between two equal phase planes along the waveguide and it is equal to:

$$\lambda_g = \frac{2\pi}{\beta} > \frac{2\pi}{k} = \lambda$$

where $k_c = \sqrt{\left(\frac{m\pi}{a}\right)^2 + \left(\frac{n\pi}{b}\right)^2}$; and $$\beta = \sqrt{k^2 - k_c^2}$$

Figure 22A:
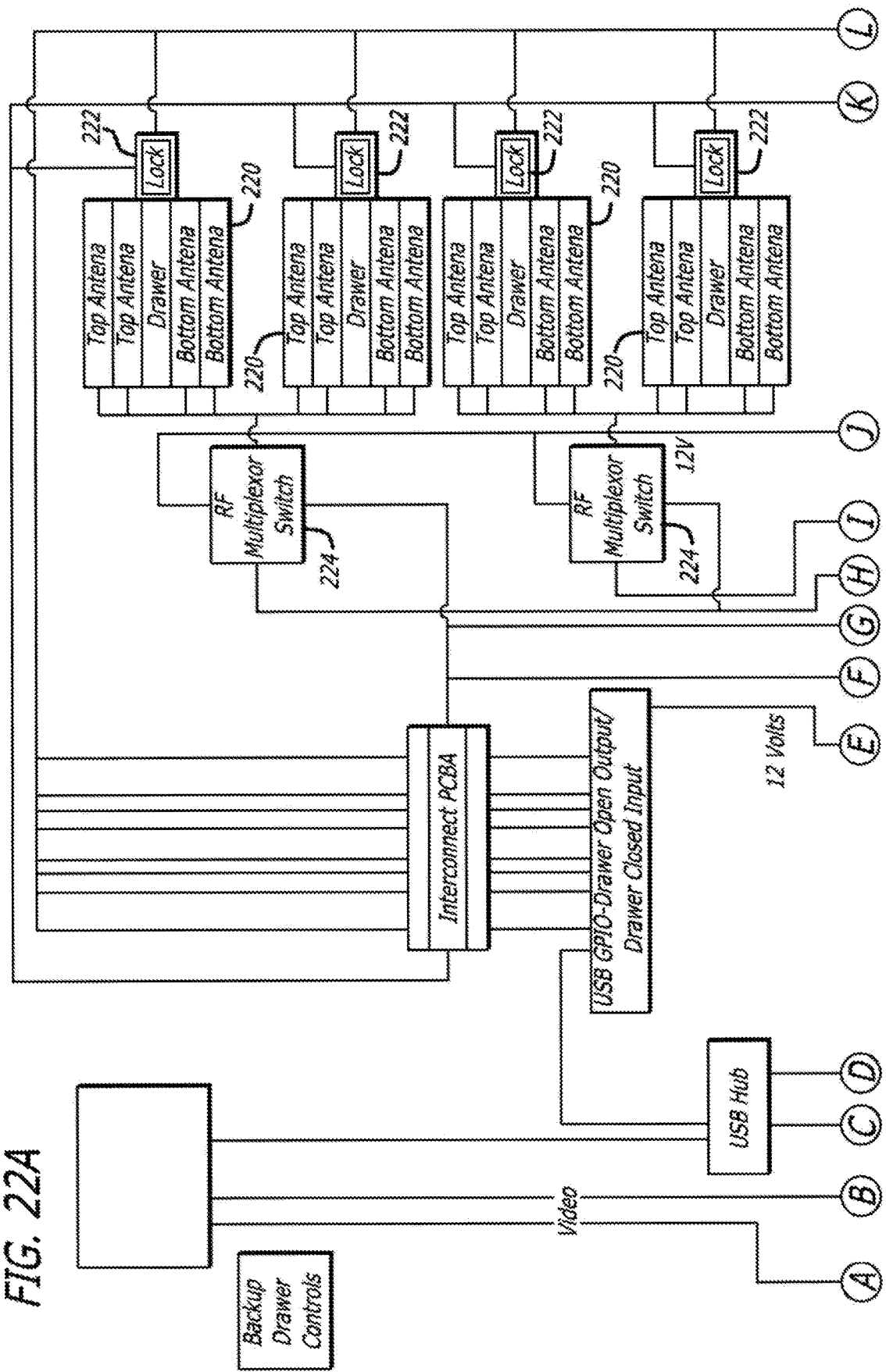
FIGS. 22A and 22B together present a block electrical and signal diagram for a multiple-drawer medical cabinet, such as that shown in FIG. 2, showing the individual multiplexer switches, the single RFID scanner, and power control.
Figure 22B:
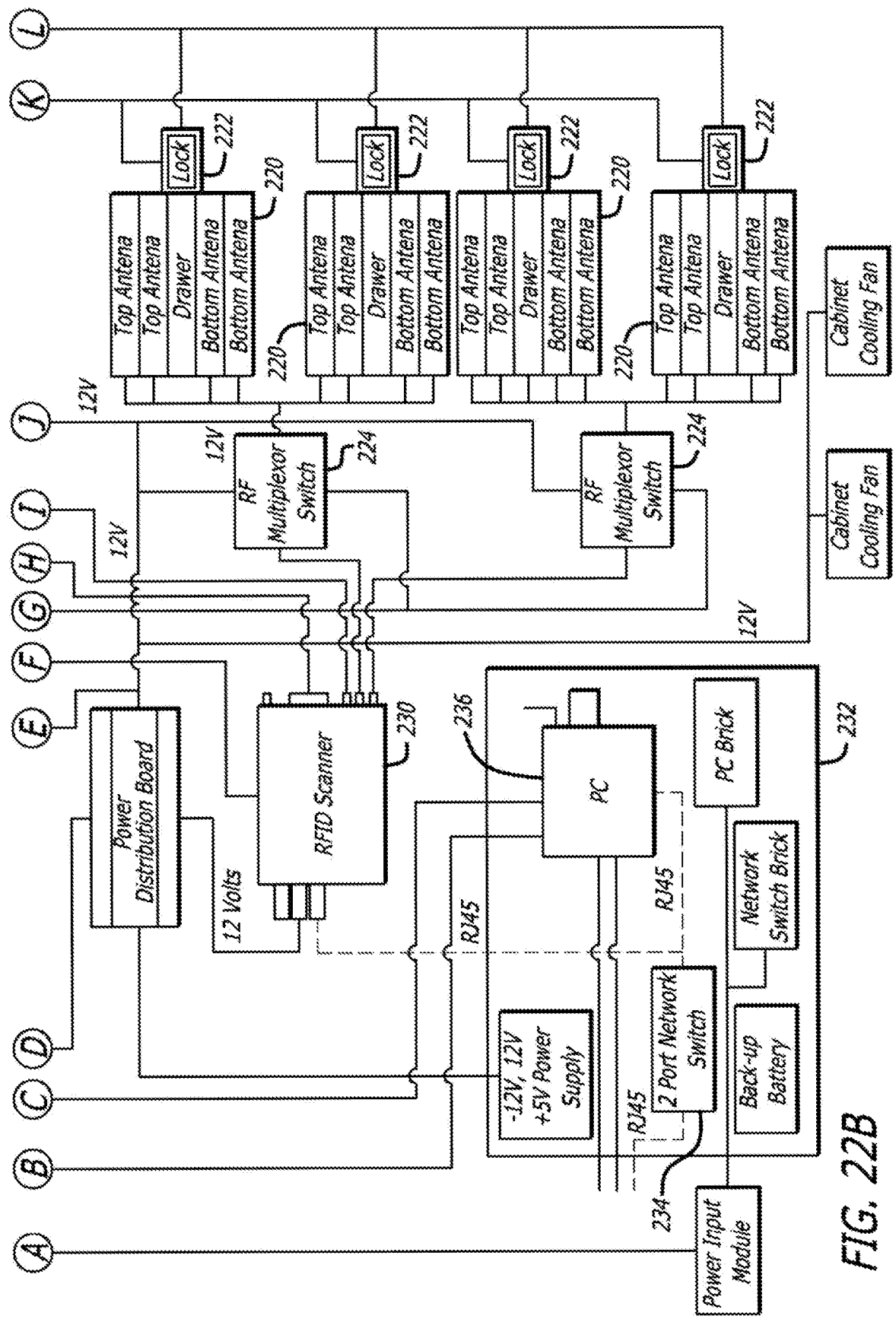
Figure 23:
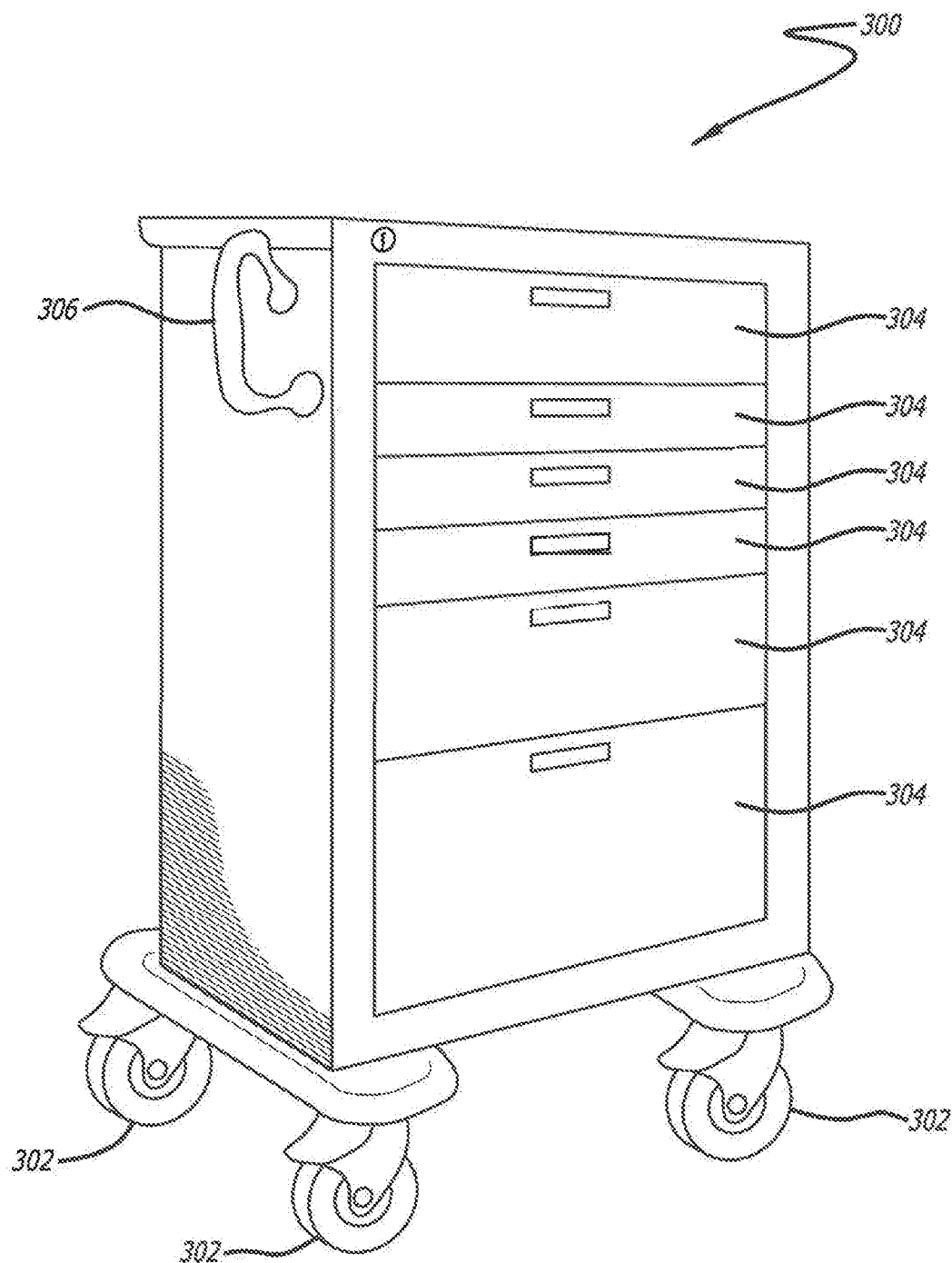
FIG. 23 is a perspective view of a hospital crash cart having a plurality drawers, each of which may contain a tray of organized medical articles or the drawer may contain loose articles. The crash cart may be supplied to support a particular use in a healthcare facility, such as the intensive care unit, pediatrics, or other.
Figure 24:
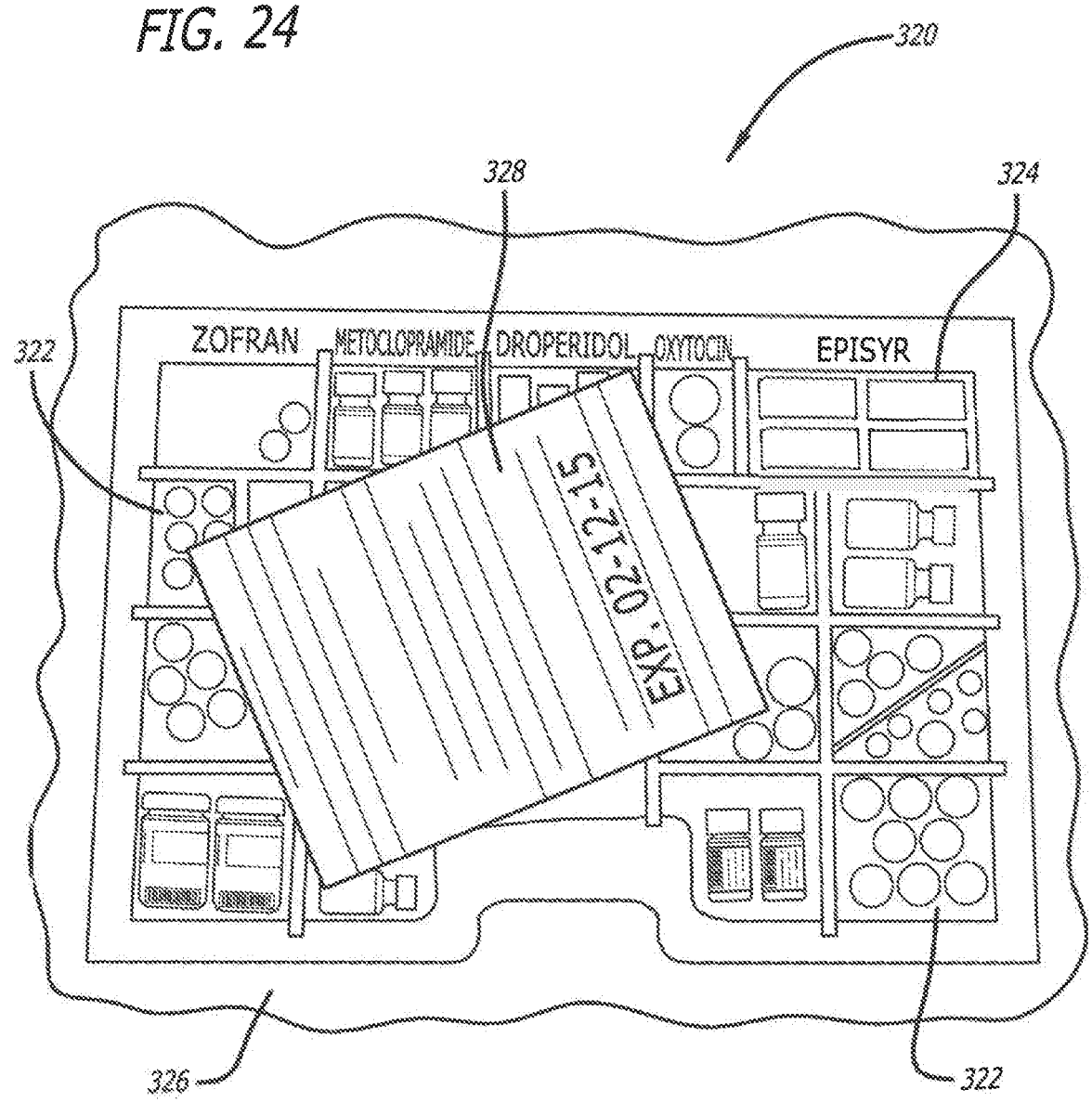
FIG. 24 is a top view of a sealed code tray showing the inventory list sealed with the medical articles of the tray. Labels have been used to advise on the particular contents of pockets of the tray.

FIGS. 22A and 22B together provide a block electrical and signal diagram for a multiple-drawer medical cabinet, such as that shown in FIG. 2. In this case, the cabinet has eight drawers 220, shown in both FIGS. 22A and 22B. Each drawer includes two top antennae, two bottom antennae and a lock with a lock sensor 222 for securing the drawer. Signals to and from the antennae of each drawer are fed through an RF multiplexer switch 224. Each RF multiplexer switch 224 in this embodiment handles the routing of RF signals for two drawers. RFID activation field and RFID received signals are fed through the respective RF multiplexer switch 224 to a main RFID scanner 230 (see FIG. 22B). The scanner 230 output is directed to a microprocessor 232 (see FIG. 22B) for use in communicating relevant information to remote locations, in this case by wired connection 234 and wireless connection 236 (see FIG. 22B). Various support systems are also shown on FIGS. 22A and 22B, such as power connections, power distribution, back up battery (see FIG. 22B), interconnection PCBA, USB support (see FIG. 22A), cooling (see FIG. 22B), and others.

In accordance with one embodiment, drawers are sequentially monitored. Within each drawer, the antennae are sequentially activated by the associated multiplexer 224. Other embodiments for the signal and electrical control systems are possible.

Figure 25:
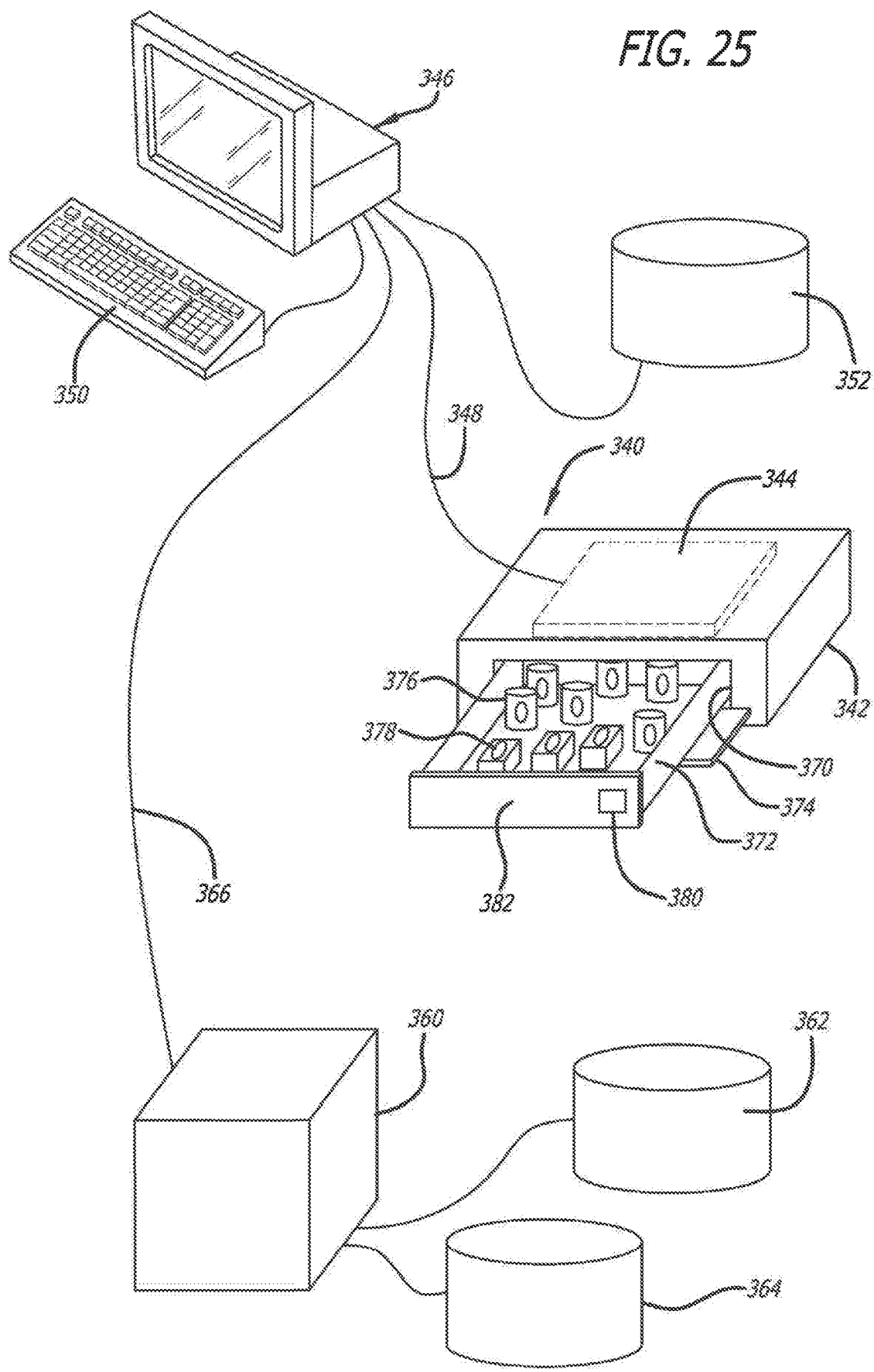
FIG. 25 is a block diagram of a scanning and inventory system in accordance with aspects of the invention in which a code tray is placed within an enclosure for scanning data carriers contained on each medical article in the tray, the scanning results compared to databases, and the results of the scanning indicating what resupply efforts area needed for the tray.

FIG. 25 shows an embodiment of an inventory management system 340 according to aspects of the invention. An enclosure 342 is shown, which in this case creates a Faraday cage in that all the walls and top and bottom are electrically conductive which isolates the enclosure by preventing (or significantly attenuating) electromagnetic energy from entering or escaping the enclosure. The enclosure is fitted with a reader 344 configured to interrogate RFID tags located within the enclosure, which may take the form of those devices shown in FIG. 1. The reader 344 is connected to a computer 346 through a connection 348. The connection 348 may be a wired connection, wireless connection, or any other suitable connection for data transfer. In one embodiment, the physical body of the computing system may be attached to the enclosure 342. The computing system 346 has a non-volatile memory 354 in which is stored at least one database ("db") which may be a local database, or other. The non-volatile memory 354 comprises one or more computer readable media within the computer system 346 and may be located within the computer itself or external to the computer. The memory is shown here as being outside the computer only for clarity of illustration in the discussion and is not meant to limit the invention in any way. In another embodiment, part or all of the local database may be held on a server 360. The computing system 346 is also connected to the remote database 360 at which is located a first remote database 362 and a second remote database 364. As in the local computer, these remote databases may be stored on a memory that is internal to the server or that is external to the server. Further, the server 360 may be located nearby the local computer 346 or may be remote therefrom. By remote, it is meant that it may be in the same room, or in the same wing, or in the same facility, or may be in the cloud. Connection 366 to the server 360 may likewise be a wired connection, wireless connection, or any other suitable connection for data transfer.

In one embodiment, the data held on the local database 352 may depend on the location/specialty/facility using computer system 346. For example, if the computer system 346 were stationed in an emergency room ("ER"), the local database 352 may hold only information or data regarding medical articles, medical containers, and other inventory most used in an ER. In one embodiment, the remote database 362 at the server 360 may serve as a main database and contain data for all medical articles, medical containers, and other inventory for all medical locations/facilities/specialties. The local database 352 may maintain a copy of the portion of data held on the remote database 362 that is most relevant to the computer system 346, but can access the remote database 362 when encountering medical items, medical containers, or other inventory for different facilities/specialties/locations.

The enclosure 342 has an opening 370 through which a tray 372 may be slid into the enclosure. The tray is placed completely within the enclosure so that the front door 374 can be closed over the opening 370 to complete the Faraday cage of the enclosure 342. The tray includes a number of medical items 376 with each one having an RFID tag 378 attached. As discussed previously, each RFID tag has a stored different identification number comprising a few bytes with a check digit. Manufacturers guarantee that each serial number is used only once. Some RFID tags have more complex codes for identifying the RFID tag. In this case, the tray 372 also has an RFID tag 280 attached to its outer surface 382. The reader 344 will read those identification numbers from the tags, communicate them to the computer which will compare them against one or more databases either locally 352 or remotely through a server 362 and/or 364. The process of using the identification numbers of the tags is discussed below.

Medical item information may include information such as name, lot code, date of manufacture, expiration date, dosage, weight, color, and an image of the medical article. In one embodiment, the identification ("ID") data may be partially made of drug codes that identify the drugs. As an example and not by way of limitation, the identification data may use the National Drug Code ("NDC") as part of its data allowing for easy identification of the attached medical item. Identification data may also have other identifying codes that establish the manufacturer, lot code, dosage, drug type, expiration date, etc.

Figure 26:
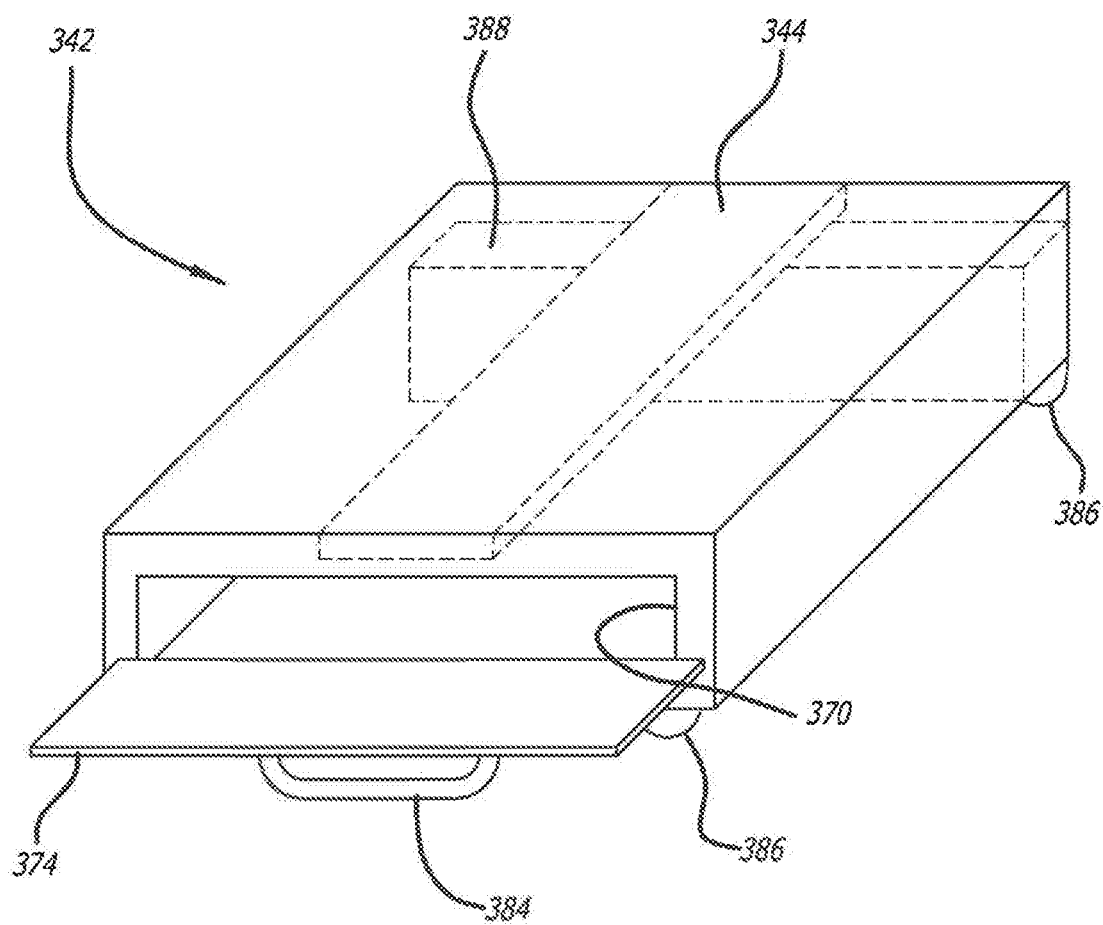
FIG. 26 is a perspective view of a scanning enclosure in accordance with aspects of the invention that may be conveniently carried to various locations in a healthcare facility to scan and inventory trays and other containers, the enclosure providing a robust electromagnetic field within its cavity to activate and read all RFID tags located therein.

Shown in FIG. 26 is an enclosure 342 formed in accordance with aspects of the invention by which it is much smaller than an enclosure sized to be resonant at the operating frequency of RFID yet the EM field within the enclosure 342 is highly robust and effective at exciting and reading all RFID tags located therein. Because inventive aspects are incorporated, the enclosure is much smaller than other enclosures and is therefore highly desirable in areas where space is limited, such as a pharmacy in a healthcare facility. Although not shown, the front door 374 includes latching hardware to retain it in a closed when it is rotated upwards and put in use. A handle 384 assists in managing the configuration of the front door. The enclosure is formed of a metallic mesh or solid metallic material to establish a Faraday cage about trays that are slid within it for scanning and inventorying. The front door in this embodiment is also formed of a metallic material and closes the Faraday cage when the door 374 is closed. The RFID reader 344 is shown in dashed lines as are the electronics and battery 388 for the enclosure. The electronics include a processor, communications, wired and wireless connections, and a local power source. In another embodiment, an AC adapter may be included for using wall power. Communications ability over networks is provided.

The approximate volume for a resonant enclosure at an RFID operating frequency of 900 MHz is 3 ft.×3 ft.×3 ft. for a total of 27 cubic feet. In one embodiment, the enclosure 342 had the dimensions of 2.25 ft. wide by 1.6 ft. long by 0.88 ft. high for an approximate volume of 3.15 cubic feet, yet achieved an equally effective EM field within the enclosure at exciting and reading all RFID tags located therein. The difference in sizes of the two enclosures makes one formed in accordance with the invention more attractive in many situations where space is limited.

Figure 27:
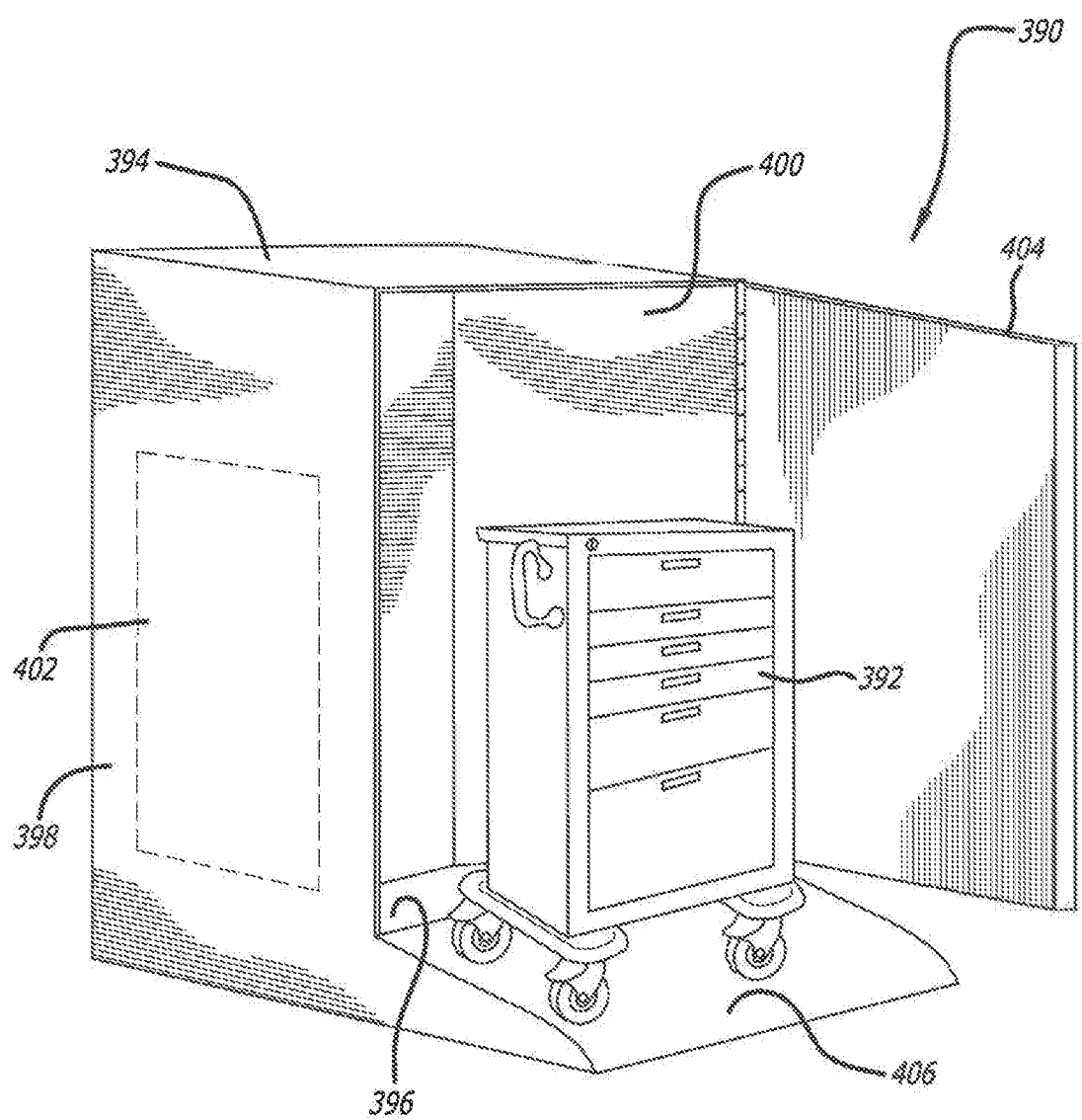
FIG. 27 is a perspective view of a much larger enclosure for crash carts that also provides an electromagnetic field within to activate, detect, and read all RFID tags in the crash cart and provide their identifications.

FIG. 27 presents another enclosure 390 of a much larger size so that it can accommodate crash carts 392 that do not include an internal RFID reader. In this embodiment, enclosure 390 has a ceiling 394 and a floor 396 which are at least partially metallic. The enclosure 390 also has two fixed side walls 398 and 400 and a back (not shown). Part of an RFID reader system 402 is shown within the enclosure. The front part 404 of the enclosure is a hinged metallic door that, when closed, completes the Faraday cage of the enclosure 390. Instead of a door, the front 404 may be a flexible panel that is also at least partially metallic. Other approaches to providing a covering over the front opening are possible, provided that they complete the Faraday cage about the crash cart 392 once it is moved completely within the enclosure 390. In an alternative embodiment, all four sides of the enclosure may be made of flexible panels so that the enclosure can more easily be moved to another location. In one embodiment, the ceiling, floor, sides, back, and front can all be fitted with RFID readers/antennas 402 so that articles within the crash cart having RFID tags can be accurately identified.

It should be noted that use of a Faraday cage is highly beneficial in healthcare facilities due to the ubiquitous presence of medical articles that have RFID tags. Without the ability to electrically isolate the tray or crash cart to be read, an RFID reader may read the RFID tags of other pharmaceuticals on shelves outside the tray or crash cart thereby giving the operator the incorrect information that those external read articles are in the tray or crash cart.

The enclosure of FIG. 27 includes a ramp 406 that may or may not be attached to the floor 396 of the enclosure. The purpose of the ramp is to facilitate rolling the crash cart into the enclosure. Other means are possible.

Figure 28:
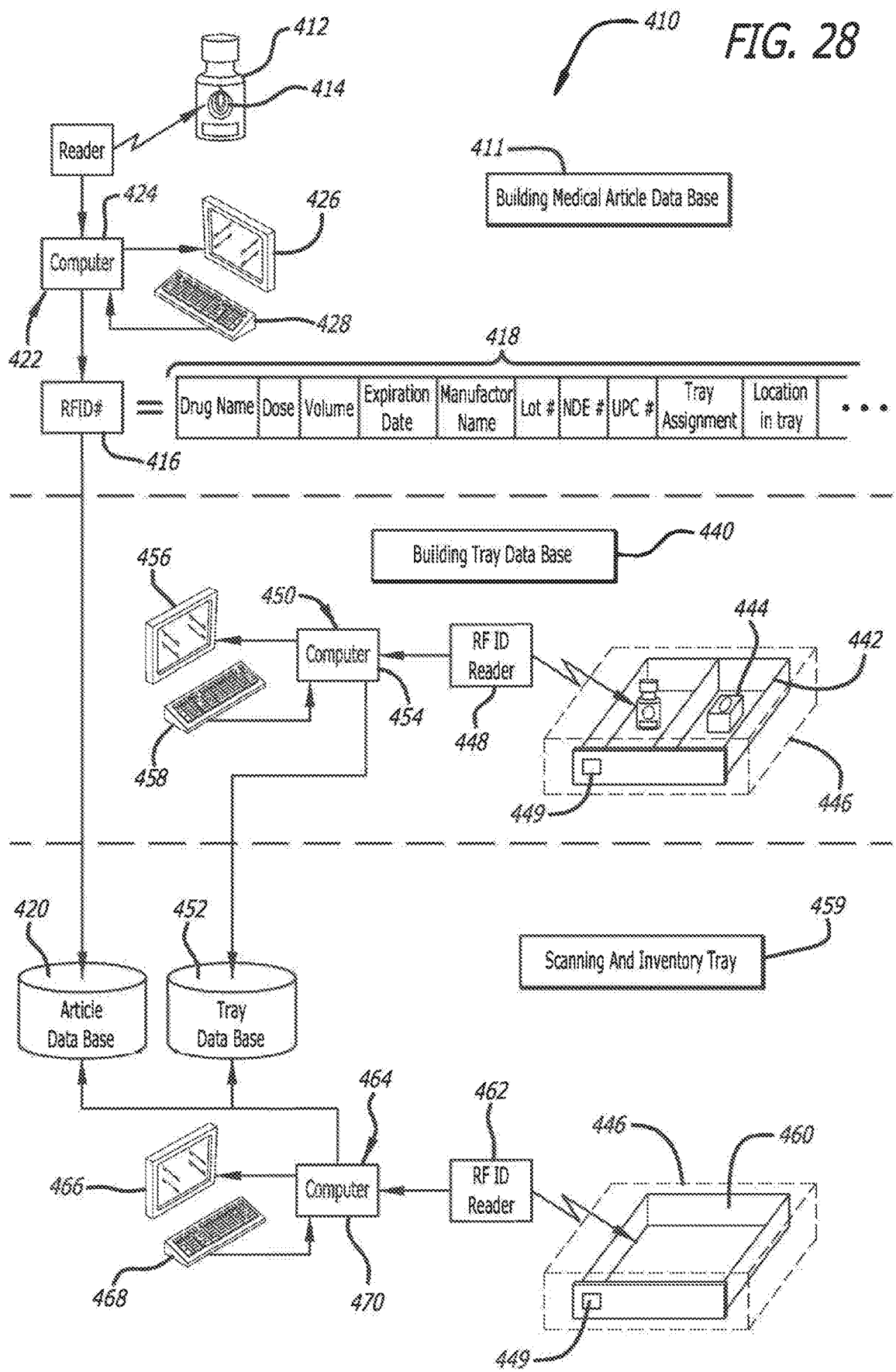
FIG. 28 is a flow chart showing embodiments of methods to build a medical articles database, build a tray database, and scan and inventory a tray to determine what changes in the medical article contents of a tray need to be made to bring the tray to the inventory level required.

FIG. 28 is a schematic diagram depicting an exemplary implementation of an inventory management system 410 according to an embodiment of the invention. Starting at the top, a database of medical articles managed by the system 410 is built 411. As an example, a medication vial 412 on which an RFID tag 414 is mounted is being registered with the system 410 by entering the RFID tag's serial number 416 along with the relevant information 418 about the medication in the vial 412 into an "articles database" 420 by the computer 422. In this case, the computer comprises a processor 424, a display 426, and an input device 428 which in this case is a keyboard. An RFID reader 430 obtains the RFID tag's serial number and assigns it to the medication information in the medication to which the RFID tag is mounted. In this case, the information about the medication comprises: the drug name, the dose, the volume, the expiration date, the manufacturer's name, the lot number, the NDC number, the UPC number, the tray number in which the medication will be store, and the location of the medication in the tray. Other information may also be included. This is then stored in the Articles Database or "Articles db" 420. Building the Articles database can be done in different ways and may be automated or may be pre-prepared by the medication manufacturer and given to the healthcare facility in electronic form. The above is repeated for all medications and other medical articles that may be placed in a tray.

The tray database, or "tray db" is built 440 in similar fashion. A tray 442 is supplied with its contents according to a Required Inventory list. Medical articles are collected and properly placed within the tray 442. In FIG. 27, only a few medical articles are shown for the purpose of clarity of the illustration. Many more articles may be placed in the tray. Each medical article within the tray includes an RFID tag 444. The fully supplied tray is placed within a Faraday cage 446, although this is not required if the tray can be sufficiently isolated from random tags, and a reader 448 reads the contents of the tray. The reader also reads an RFID tag 449 attached to the tray 442 itself. A computer 450 receives the read tag numbers and stores them as a tray database 452. In the tray database, the tray RFID tag identification is connected with the type and name of the tray and the RFID tag numbers are connected with the medical articles placed in the tray. Trays may have certain categories, such as ER, or ICU, or pediatric, or other, and the tray database will indicate that category for the RFID no. of the tray RFID tag. As in the other systems, the computer here includes a processor 454, a display 456, and an input device 458 which in this case is a keyboard. The computer also comprises both random access memory and non-volatile memory, as do the other computers shown and described herein. In one embodiment, the tray database is relational in that it points to the medical articles database to obtain more detailed information about its inventory.

While the embodiment herein described refer to "trays," other container types may function equally well. It is not meant to confine the invention to any particular type of container unless so indicated.

A scanning and inventory system is shown at the bottom of FIG. 28 and includes positioning the tray to be inventoried 460 within a RFID reader enclosure 446 that provides a Faraday cage within itself. The tray to be inventoried 460 is positioned entirely within the Faraday case part of the enclosure 446 so that no external RFID tags will be read by the reader. 462. After closing the enclosure, the RFID reader 462 scans the tray 460, including the RFID tag on the tray itself 490 and the tags on each of the medical articles within the tray. The identification numbers of each of the read RFID tags is communicated by the reader to a computer 464 similar to the other computers 424 and 450 described above. The computer includes a display 466, an input device 468 which, in this case, is a keyboard, and a processor 470 forming part of the computer 464. In this embodiment, the computer processor 470 compares the tray RFID tag serial no. to those stored in the tray database 452. If found in the tray database, that tray's inventory will be provided for further processing, as described below.

In accordance with an aspect of the invention, the enclosure described above; i.e., enclosure 446, is a RFID scanning enclosure (see FIG. 26) configured with the robust EM field in accordance with the inventive aspects above. In particular, the enclosure may be configured as shown in FIGS. 13-17 and perform as described to achieve the robust field for detecting, activating, and reading all RFID tags within the enclosure.

Figure 29:
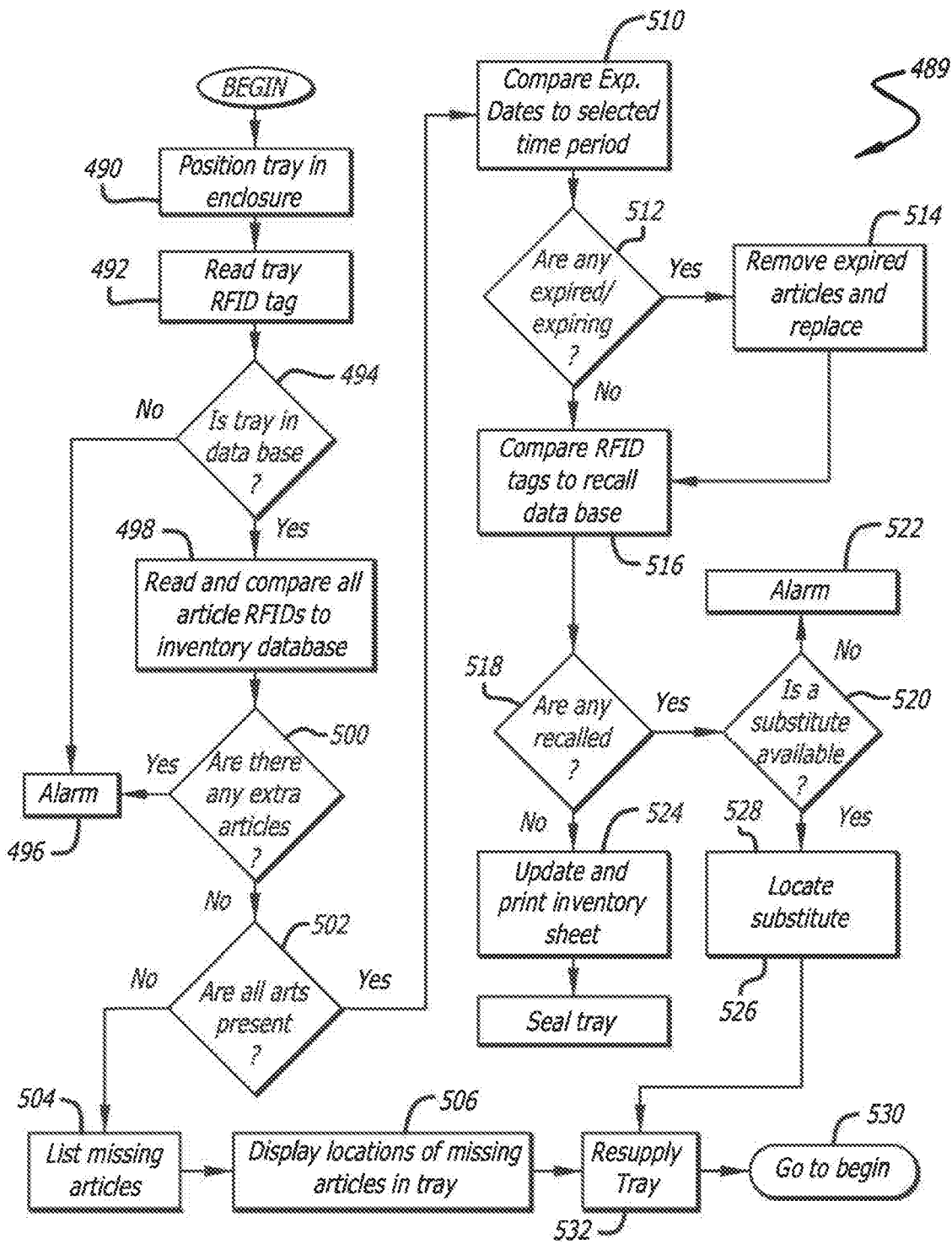
FIG. 29 is a flow chart of an embodiment of a method for scanning a tray, determining its contents, and indicating any changed needed to supply the tray according to a predetermined inventory; also shown is a method for scanning medical articles of the tray for expired and recalled articles.

Referring now to FIG. 29, a flow chart is provided that describes an embodiment of a method of scanning and inventorying a code tray in accordance with aspects of the invention. A tray is positioned in an enclosure 490 such as that provided by FIGS. 13-17 and 26. An RFID reader then reads the RFID tag of the tray 492. The serial number of the tray RFID tag is then automatically compared to a tray database to determine if this scanned tray is in the database 494. If the tray is not in the database, an alarm is provided 496. If the tray is in the tray database, all RFID tags of medical articles in the tray are read, and the names and details of the medical article to which they are attached are automatically compared 498 to the Required Inventory list of that tray. A determination is made if there are any extra articles in the tray that are not included in the stored tray database 450. The access by the program of multiple databases may be needed to perform this step. If extras are detected, an alarm is provided 496 so that those extra articles may be removed from the tray. If no extra articles are found, a determination is made if all required inventory articles are in the tray 452. If articles are missing, a list of the missing articles is automatically displayed 504 and may be printed as needed. In one feature of an embodiment, the computer program performing the above steps may display 506 a graphical image of the tray 506 and indicate where in the tray the missing articles should be placed. Such an image is shown in FIG. 31 where a blinking asterisk 508 indicates where a medical article should be placed. Many different ways may be employed to assist in the placement of medical articles in the tray. Replacements for the missing medical articles are collected and the tray is re-supplied 532 by positioning the medical articles at the proper location in the tray.

If all articles are present in the tray, the computer program may be informed of such and formalities are then conducted. The electronic record for the particular tray is updated and an inventory sheet for the tray is printed for inclusion with the tray. The tray is then sealed and taken to the assigned location in the healthcare facility for possible future use. However, in the event that the operator of the computer program performing the described scanning and inventory, the expiration dates of all medical articles in the tray may be checked. From the scan of the medical articles, the inventory dates are compared against the present date 510. In another aspect of the invention, the program may display a screen asking the operator which time period of expiration is desired for checking. Turning now to FIG. 30, a screen shot 550 of the program is reproduced showing that in this embodiment, a drop-down list 552 of expiration periods is available to the operator. By selecting any one of the periods, the program will then search for and list 554 below the selected period all medical items expiring in that time period. If any medical items are listed 554, they may be found in the tray and replaced 514.

The program next proceeds to determining if any scanned medical articles have been recalled 514 by the manufacturer or the FDA, or otherwise. The comparison of the identification of the detected medical articles in the tray are compared to a "Recalled" database and if any articles match recalled articles, it is then determined if a substitute medical article exists 520. If none exists, an alarm is provided 522. If a substitute article does exist, a substitute is located 528 and supplied to the tray 532. If no recalled articles exist in the tray, in this embodiment, the inventory of the tray is updated in the database 524; i.e., that a scan and verification of contents was just made, an inventory sheet is printed, and the tray is sealed 526. The tray may now be moved to a location in the healthcare facility where it may be put to use.

However, in the case above where medical articles had to be added to the tray for missing, expired, or recalled items, a rescan if performed 530 in this embodiment. Such scans, rescans, replacements, expiration, and recalls are all noted for one or more databases kept by the inventory re-supply system in accordance with the invention. Because of the data captured in scans and in the databases built by embodiments, many searches for medical articles may be performed. For example, if a pharmacy were concerned to locate all medications or other medical articles having an expiration date within one month (see FIG. 30), a search of one or more databases of the embodiment above can be made to find such expiring articles. Another search on a database may be then made to track the position of those expiring articles; i.e., to determine if they are in a tray, and if so, which tray it is, and in what pocket of the tray. Such trays with expiring articles may be gathered, and the re-supply may be made.

Figure 32:
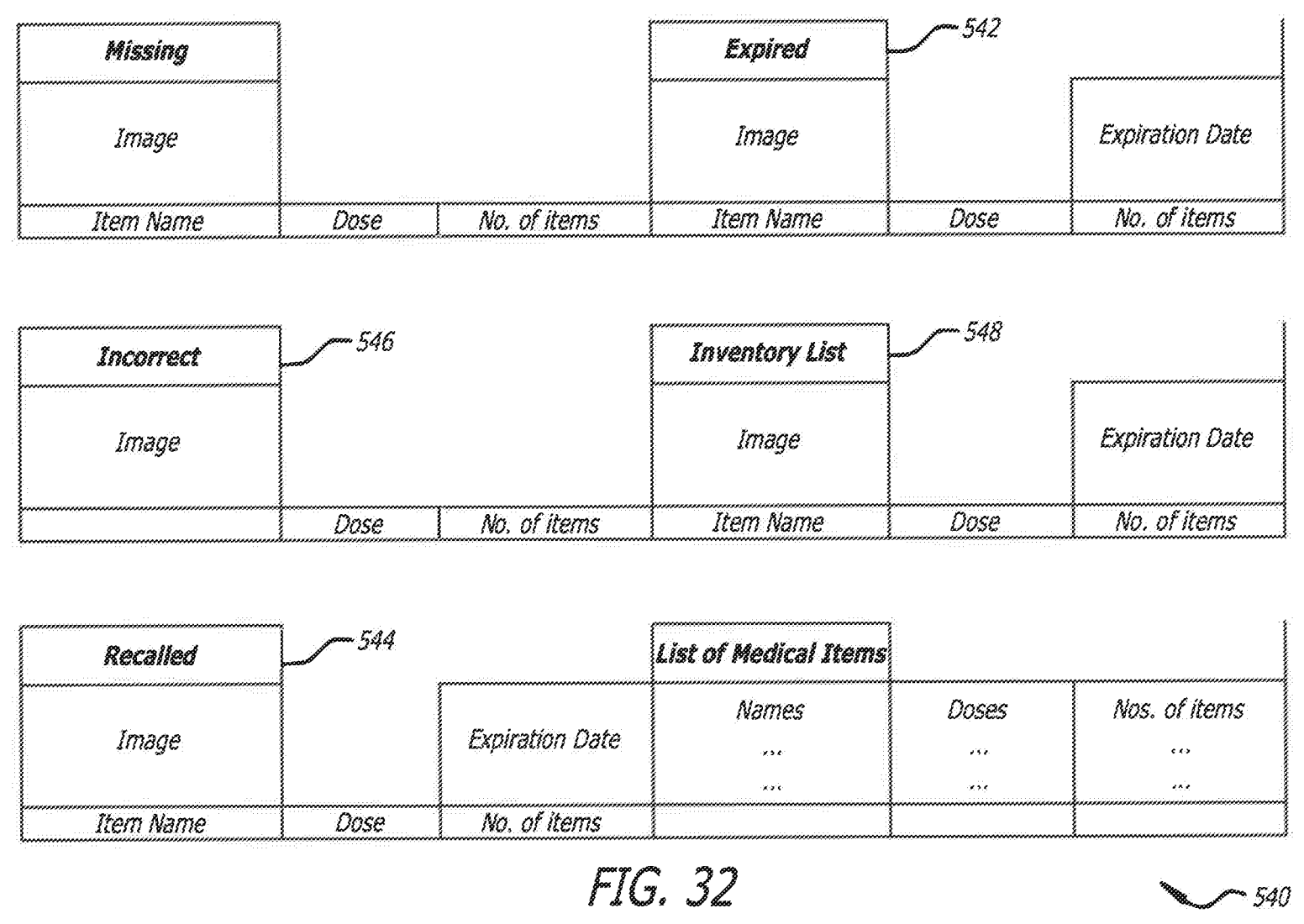

Referring now to FIG. 32, there is shown a computer program screen shot 540 of a listing of the articles detected in a tray during a scan of that tray in accordance with aspects of the invention. Various categories are shown including expiration 542 and recall 544. Incorrect articles 546 may be listed and for convenience, the entire Required Inventory list can be displayed as well as a check mark next to each one that is present and not expired. Many different forms of the display of results from scanning a tray, crash cart, or other container may be provided. FIG. 32 is just one embodiment.

Multiple databases may be employed in the system and method described above. According to one embodiment, the system 340 (FIG. 25) and the method 489 (FIG. 29) may search one or more databases of medical article information matching the identification data. In one embodiment the identification data may be found in multiple databases each database containing different information. As by way of example and not limitation, the name, dosage, lot code and expiration date may be on one database while recall status may be in another database. In another embodiment all the medical item information may be held in one database which may have its information on other databases as backup. In yet another embodiment, medical item information may be stored on a local database within the computing device connected to the enclosure, and the local database may be updated periodically over a network connection from one or more remote databases.

The alarms that are provided may be done so visually, such as by displayed on a computer screen, audibly, such as through speaker sounds, and/or tactile by vibrations. Other means or combinations of means for communicating an alarm condition may be used.

According to one embodiment, the data files within the databases containing medical information may take the form of a comma separated value list which may have multiple data fields and may look like "Name, Dosage, and Expiration." Other serialized formats may be used to contain the data, including but not limited to, Extensible Markup Language (XML), JavaScript Object Notation (JSON), etc. The data may also take the form of proprietary file formats created by medical article manufacturers. Furthermore, the data may contain a pointer or addresses to additional data providing additional information about the medical item or medical container. One example of additional information may be a data representation of a medical item's image. There are many different file or data formats that may be used to store medical information and any suitable format is contemplated within this invention. In one embodiment, multiple datasets using different data formats containing medical item information may be used, each for a particular medical item manufacturer or distributor. A system may be configured to identify particular datasets based on the identification data from a data carrier (such as an RFID tag). In an alternative embodiment, a single data format may be used across all medical items independent of manufacturers.

The inventory management system in accordance with the invention may display a list of every medical item missing from the medical container, any additional medical items not within the inventory list, any drugs with incorrect dosages, and any expiration date and/or status of every medical item within the container that is attached to a data carrier with identification data. In one embodiment as discussed above, the system may also display an image of each medical article that is missing, additional, incorrect dosage, expired, recalled, etc. That image of the medical article may make it easier for operators to find the displayed medical article or articles in the medical container. The image may be a visual representation of the medical article or its container which may include label colors. In an alternative embodiment, a diagram of the medical container may be provided, and the location of the medical article in the medical container may be highlighted in the diagram.

In one embodiment, an inventory management system and method in accordance with the invention may use color indicators to communicate any differences/anomalies with the articles within the medical container and the inventory list. The inventory management system and method may also provide expiration indicators. As an example, but not by way of limitation, expiration indicators may include displaying a countdown of the number of days left until expiration of a medical article. In another embodiment, a color indicator using color gradients or color coding may indicate the life of the medical article such as green to red, white to black, etc. Each end of the color/gradient spectrum may represent the life or expiration of the a medical article.

In further regard to FIG. 32, the display may use multiple windows. Each window may display different information regarding the contents of the scanned medical container such as a window for missing articles, a window for expired articles, a window for incorrect or additional articles not part of the container's inventory, a window for an inventory list, a window for recalled articles, and a window for aggregated information. Each window may have an image display, name, dosage, number of articles, and expiration or recall status indicator. Each window may also have a scroll bar for additional data that does not fit in a single window. In an alternative embodiment, a single window may be used and the user may be provided with the ability to select what is displayed in the window.

In one embodiment, the inventory management system may allow for registering or creating specialized and/or individualized medical containers and inventories for entry into one or more databases. A user may fill a medical container with the correct number of medical articles (attached with data carriers) intended for the medical container. The user may insert the medical container into the enclosure of the inventory management system, such as described above in FIG. 28 at numeral 41. A user may instruct the inventory management system 410 through an input device 428, to register the container under a certain category, including specialized and/or individualized categories. The system may read identification data from every data carrier within the enclosure. In one embodiment, a data carrier is attached to the medical container itself. The system 410 may search a database for medical information associated with each identification data read from the data carriers within the container. The system builds an inventory list from the accessed medical article information and stores it on the database in association with the identification data of the specialized medical container.

The computers 422, 450 and 464 of FIG. 28 may take any suitable form, including but not limited to, an embedded computer system, a system-on-chip (SOC), a single-board computer system (SBC) (such as, for example, a computer-on-module (COM) or system-on-module (SOM)), a laptop or notebook computer system, a smart phone, a personal digital assistant (PDA), a server, a tablet computer system, a kiosk, a terminal, a mainframe, a mesh of computer systems, etc. The computers may be a combination of multiple forms. The computers may include one or more computer systems, be unitary or distributed, span multiple locations, span multiple systems, or reside in a cloud (which may include one or more cloud components in one or more networks).

In one embodiment, the computers 422, 450 and 464 of FIG. 28 may include one or more processors, memory, storage, an input/output (I/O) interface 3004, a communication interface, and a bus. Although this disclosure describes and illustrates a particular computer system having a particular number of particular components in a particular arrangements, this disclosure contemplates other forms of computer systems having any suitable number of components in any suitable arrangement.

In one embodiment, processor includes hardware for executing instructions, such as those making up software. Herein, reference to software may encompass one or more applications, byte code, one or more computer programs, one or more executable, one or more instructions, logic, machine code, one or more scripts, or source code, and vice versa, where appropriate. As an example and not by way of limitation, to execute instructions, processor may retrieve the instructions from an internal register, an internal cache, memory or storage; decode an execute them; and then write one or more results to an internal register, an internal cache, memory, or storage. In one embodiment, processor may include one or more internal caches for data, instructions, or addresses. Memory may be random access memory (RAM), static RAM, dynamic RAM or any other suitable memory. Storage maybe a hard drive, a floppy disk drive, flash memory, an optical disk, magnetic tape, or any other form of storage device that can store data (including instructions for execution by a processor).

In one embodiment, storage may be mass storage for data or instructions which may include, but not limited to, a HDD, solid state drive, disk drive, flash memory, optical disc (such as a DVD, CD, Blu-ray, and the like), magneto optical disc, magnetic tape, or any other hardware device which stores may store computer readable media, data and/or combinations thereof. Storage may be internal or external to computer system.

The term "operationally responsive" is used herein for the purpose of additional clarity. It is believed that one skilled in the art would recognize that an RFID device built for operation at a particular nominal frequency would not be considered operationally responsive at a much different frequency, even though it may function somewhat, but at an unacceptable or "nonoperational" level. Therefore the term "not responsive" should be sufficient but for the avoidance of doubt, applicant has used the term not operationally responsive, but believes that it is synonymous with not responsive.

In one embodiment, input/output (I/O) interface, includes hardware, software, or both for providing one or more interfaces for communication between computer system and one or more I/O devices. Computer systems may have one or more of these I/O devices, where appropriate. As an example but not by way of limitation, an I/O device may include one or more mouses, keyboards, keypads, cameras, microphones, monitors, display, printers, scanners, speakers, cameras, touch screens, trackball, trackpad, biometric input device or sensor, or the like.

In still another embodiment, a communication interface includes hardware, software, or both providing one or more interfaces for communication between one or more computer systems or one or more networks. A communication interface may include a network interface controller (NIC) or a network adapter for communicating with an Ethernet or other wired-based network or a wireless NIC or wireless adapter for communications with a wireless network, such as a local wireless network. In one embodiment, bus includes any hardware, software, or both coupling components of a computer system to each other.

"Medical article" is used in this document its broadest sense. For example, a medical article can be a medical device, a pharmaceutical drug, a lab specimen, a blood product, a human organ, a hospital scrub, a surgical instrument, a medical implant, a sponge or gauze pad, a healthcare institution code tray containing drugs to be tracked, and a code tray containing medical devices to be tracked.

As has been described, the various embodiments of the present invention relates to a system and method for medical article inventory and management. For purposes of explanation, specific nomenclature is set forth to provide a thorough understanding of the present invention. Description of specific applications and methods are provided only as examples. Various modifications to the embodiments will be readily apparent to those skilled in the art and the general principles defined herein may be applied to other embodiments and applications without departing from the spirit and scope of the invention. Thus the present invention is not intended to be limited to the embodiments shown, but is to be accorded the widest scope consistent with the principles and steps disclosed herein.

Although RFID tags are used herein as an embodiment, other data carriers that communicate through electromagnetic energy may also be usable.

While the invention has been described in connection with what is presently considered to be the most practical and preferred embodiments, it is to be understood that the invention is not to be limited to the disclosed embodiments and elements, but, to the contrary, is intended to cover various modifications, combinations of features, equivalent arrangements, and equivalent elements included within the spirit and scope of the appended claims.

Unless the context requires otherwise, throughout the specification and claims that follow, the word "comprise" and variations thereof, such as, "comprises" and "comprising" are to be construed in an open, inclusive sense, which is as "including, but not limited to."

While particular embodiments of the present invention have been described, it is understood that various different modifications within the scope and spirit of the invention are possible. The invention is limited only by the scope of the appended claims.

What is claimed is:

1. A medical storage container supply system configured to store multiple medical articles in a plurality of pockets, the medical container supply system using identification devices that are responsive to electromagnetic (EM) energy, the medical container supply system comprising:
   an enclosure having an internal storage area, the enclosure further having electrically conductive walls that surround the internal storage area and a medical storage container and its inventory when the medical storage container is placed within the internal storage area of the enclosure;
   wherein the medical storage container includes an EM energy identification device and medical articles stored within the storage container include EM energy identification devices, wherein each of the identification devices are responsive to EM energy to provide identification data;
   a probe disposed within the enclosure, the probe configured to inject EM energy into the enclosure to activate EM energy devices, wherein the probe is further configured to receive identification data provided by the identification device of the medical storage container and the identification devices of the medical articles stored in the medical storage container when they are located in the enclosure;
   an inventory list having an inventory of medical articles to be located in the medical storage container;
   a non-volatile memory on which is stored the inventory list of the medical storage container, and a diagram showing in which pockets medical articles are to be stored;
   a display; and
   a processor programmed to receive the identification data provided by the identification device of the medical storage container, to access the non-volatile memory to locate the inventory list of the identified medical storage container, to receive identification data provided by the identification devices of the medical articles located in the storage container in the enclosure, and to compare the identifications of medical articles to the inventory list of medical articles for the medical storage container to determine any variations between the actual inventory in the medical storage container from the inventory list;

wherein the processor is further programmed to show the layout of the pockets in the identified medical storage container and to provide an indicator that shows in which pocket a particular medical article is placed; and wherein the processor is further programmed to control the display to display multiple windows of data about the contents of an identified medical storage container wherein each window displays different information regarding the contents of the identified medical storage container, including at least one of:

a window for missing medical articles;

a window for extra or additional or incorrect medical articles not part of the storage medical container's inventory list;

a window for an inventory list; and a window for aggregated information.

2. The medical storage container supply system of claim 1 wherein the processor is further programmed to control the display to display a list of missing medical articles.

3. The medical storage container supply system of claim 1 wherein the processor is further programmed to control the display to display a diagram of the identified medical storage container to highlight locations on the diagram where missing medical articles should have been located.

4. The medical storage container supply system of claim 1 wherein the processor is further programmed to control the display to display the inventory list on the display with marks on the displayed inventory list indicating what medical articles were found to be present in the medical storage container.

5. The medical storage container supply system of claim 1 wherein the processor is further programmed to control the display to display graphical images of missing medical articles.

6. The medical storage container supply system of claim 1 wherein:

the non-volatile memory also comprises a database of diagrams showing locations where medical articles are to be located in the medical storage container;

the processor is further programmed such that if the processor determines that medical articles are missing from an identified medical storage container, the processor accesses the database of diagrams of the locations of medical articles in the medical storage container; and the processor controls the display to display a diagram of the location in the medical storage container in which the missing medical articles should be placed.

7. The medical storage container supply system of claim 1 wherein the enclosure includes an opening having a size large enough so that a medical storage container presently located in the internal storage area of the enclosure can be removed from the enclosure and a different medical storage container can be placed in the internal storage area of the enclosure in place of the one removed.

8. A method of supplying a medical storage container having a plurality of pockets by reading an identification device that is attached to the medical storage container and for reading identification devices attached to medical articles located in the medical storage container to manage the inventory if the medical storage container, each of the identification devices being responsive to electromagnetic (EM) energy in response to which the identification devices provide identification data, the medical storage container and medical articles being located within an internal storage area of an enclosure, the enclosure having electrically conductive walls that surround the internal storage area and a medical storage container holding medical articles with associated identification devices placed therein, the method comprising:

positioning a medical storage container within the internal storage area of the enclosure, the storage container having an identification device identifying the storage container, the medical storage container containing medical articles, wherein each of the medical articles located therein having an associated identification device, the identification devices being responsive to electromagnetic (EM) energy to transmit identification data;

injecting EM energy into the enclosure from a location within the enclosure;

storing an electronic inventory list of the medical storage container on a non-volatile memory; and receiving the identification data of the medical storage container by a processor, locating the inventory list of the identified medical storage container in the non-volatile memory by the processor through the identification of the medical storage container, receiving identification data of the medical articles located in the medical storage container, locating the details of the medical articles in the identified medical storage container by the processor in the non-volatile memory through the identification data of the medical articles, comparing the details of the identified medical articles against the inventory list of the medical storage container in which the identified medical articles are located, and based on the step of comparing, determining any differences between the medical articles that are in the medical storage container from the inventory list; and showing the layout of the pockets in the identified medical storage container and providing an indicator that shows in which pocket a particular medical article is placed;

wherein if the identification data of the medical storage container is not found in the database on the memory, providing an alarm.

9. The method of supplying a medical storage container of claim 8 wherein if it is determined that there are missing medical articles from the identified medical storage container, then controlling a display to display a list of the missing medical articles.

10. The method of supplying a medical storage container of claim 8 wherein if an extra medical article is detected, providing an alarm whereby the extra article may be removed from the medical storage container.

11. The method of supplying a medical storage container of claim 8 further comprising controlling a display to display graphical images of missing medical articles.

12. The method of supplying a medical storage container of claim 8 wherein if it is determined that medical articles are missing from the identified medical storage container, then displaying a diagram of the location in the medical storage container in which the missing medical articles should be located.

13. The method of supplying a medical storage container of claim 8 wherein when identification data of the identified medical storage container and the identification data of the identified medical articles in the medical storage container are received, displaying a list with marks on the list indicating what medical articles were found to be present in the medical storage container.

14. The method of supplying a medical storage container of claim 8 further comprising displaying a diagram of the medical storage container and highlighting the locations of missing medical articles in the medical storage container in the diagram.

15. The method of supplying a medical storage container of claim 8 further comprising removing a medical storage container presently located in the internal storage area of the enclosure through an opening in the enclosure and replacing the removed medical storage container with a different medical storage container.

16. A method of supplying a medical storage container having a plurality of pockets by reading an identification device that is attached to the medical storage container and for reading identification devices attached to medical articles located in the medical storage container to manage the inventory of the medical storage container, each of the identification devices being responsive to electromagnetic (EM) energy in response to which the identification devices provide identification data, the medical storage container and medical articles being located within an internal storage area of an enclosure, the enclosure having electrically conductive walls that surround the internal storage area and a medical storage container holding medical articles with associated identification devices placed therein, the method comprising:

positioning a medical storage container within the internal storage area of the enclosure, the storage container having an identification device identifying the storage container, the medical storage container containing medical articles, wherein each of the medical articles located therein having an associated identification device, the identification devices being responsive to electromagnetic (EM) energy to transmit identification data;

injecting EM energy into the enclosure from a location within the enclosure;

storing an electronic inventory list of the medical storage container on a non-volatile memory;

receiving the identification data of the medical storage container by a processor, locating the inventory list of the identified medical storage container in the non-volatile memory by the processor through the identification of the medical storage container, receiving identification data of the medical articles located in the medical storage container, locating the details of the medical articles in the identified medical storage container by the processor in the non-volatile memory through the identification data of the medical articles, comparing the details of the identified medical articles against the inventory list of the medical storage container in which the identified medical articles are located, and based on the step of comparing, determining any differences between the medical articles that are in the medical storage container the inventory list; and showing the layout of the pockets in the identified medical storage container and providing an indicator that shows in which pocket a particular medical article is placed;

further comprising displaying multiple windows of data about the contents of an identified medical storage container wherein each window displays different information regarding the contents of the identified medical storage container, including at least one of:

a window for missing medical articles;
a window for extra, incorrect, or additional medical articles not part of the medical storage container's inventory list;
a window for a required inventory list; and
a window for aggregated information.

17. A medical storage container supply system for reading an identification device that is attached to a medical storage container having a plurality of pockets and for reading identification devices attached to medical articles located in the medical storage container to manage the inventory of the storage container, each of the identification devices being responsive to electromagnetic (EM) energy to provide identification data, the system comprising:

an enclosure having an internal storage area, the enclosure further having electrically conductive walls that surround the internal storage area and a storage container in which medical articles are located, and also having an opening through which a storage container located in the internal storage area can be replaced with a different storage container, each medical article having an associated identification device;

a probe disposed within the enclosure, the probe configured to inject EM energy into the enclosure;

a medical storage container having an identification device identifying the medical storage container, the storage container being located within the internal storage area of the enclosure and containing medical articles, each of which having an associated identification device identifying that medical article, the identification devices being responsive to EM energy to provide identification data;

wherein the probe is further configured to receive identification data provided by identification devices of the medical storage container and the medical articles stored in the medical storage container when they are located in the enclosure;

an inventory list having an inventory of medical articles to be located in the medical storage container;

a non-volatile memory on which is stored the inventory list of the medical storage container;

a display; and a processor programmed to receive the identification data provided by the identification device of the medical storage container, to access the non-volatile memory to locate the inventory list of the identified medical storage container, to receive identification data provided by the identification devices of the medical articles located in the storage container in the enclosure, and to compare the received identifications of medical articles to the inventory list of required medical articles for the medical storage container to determine from the comparison at least one of whether there are missing medical articles not in the medical storage container that are on the required inventory list, and whether there are extra medical articles in the medical storage container but not on the required inventory list;

wherein the processor is further programmed to control the display to display the inventory list on the display with marks on the displayed inventory list indicating either what medical articles were found to be present in the medical storage container, or what medical articles were found to be missing in the medical storage container;

wherein if the identification data of the medical storage container is not found in the database on the non-volatile memory, the processor is programmed to provide an alarm; and wherein the processor is further programmed to show the layout of the pockets in the identified medical storage container and to provide an indicator that shows in which pocket a particular medical article is placed.

\* \* \* \* \*